(12) United States Patent
Ferreira et al.

(10) Patent No.: US 7,902,425 B2
(45) Date of Patent: Mar. 8, 2011

(54) PLANTS HAVING CHANGED DEVELOPMENT AND A METHOD FOR MAKING THE SAME

(75) Inventors: Paulo Cavalcanti Gomes Ferreira, Rio de Janeiro (BR); Adriana Silva Hemerly, Rio de Janeiro (BR)

(73) Assignees: Cropdesign N.V., Zwijnaarade (BE); Universidade Federal Do Rio De Janeiro, Rio de Janeiro (BR)

( * ) Notice: Subject to any disclaimer, the term of this patent is extended or adjusted under 35 U.S.C. 154(b) by 556 days.

(21) Appl. No.: 10/526,221

(22) PCT Filed: Sep. 5, 2003

(86) PCT No.: PCT/EP03/10087
§ 371 (c)(1),
(2), (4) Date: Nov. 15, 2005

(87) PCT Pub. No.: WO2004/029257
PCT Pub. Date: Apr. 8, 2004

(65) Prior Publication Data
US 2006/0162023 A1    Jul. 20, 2006

(30) Foreign Application Priority Data

Sep. 5, 2002   (WO) .................. PCT/EP02/10265

(51) Int. Cl.
*C12N 15/82* (2006.01)
*A01H 5/00* (2006.01)
*A23K 1/14* (2006.01)

(52) U.S. Cl. ......... 800/290; 800/298; 800/306; 800/312; 800/314; 800/317.3; 800/320; 800/320.1; 800/320.2; 800/320.3; 800/322; 435/468; 426/615; 426/635

(58) Field of Classification Search .................. None
See application file for complete search history.

(56) References Cited

U.S. PATENT DOCUMENTS 5,750,862 A * 5/1998 John ........................... 800/320

FOREIGN PATENT DOCUMENTS

| WO | 01/02430 | | 1/2001 |
| WO | WO 01/02430 | * | 1/2001 |
| WO | 02/38599 | | 5/2002 |

OTHER PUBLICATIONS

Perez-Perez J.M. et al. Specialization of CDC27 function in the *Arabidopsis thaliana* anaphase-promoting complex (APC/C). Plant J. Jan. 2008;53(1):78-89. Epub Oct. 17, 2007.*
Blilou, Ikram et al.: "The *Arabidopsis* HOBBIT gene encodes a CD C27 homolog that links the plant cell cycle to progression of cell differentiation" Genes and Development, vol. 16, No. 19, pp. 2566-2575, Oct. 1, 2002. XP002265006.

* cited by examiner

*Primary Examiner* — Cynthia Collins
(74) *Attorney, Agent, or Firm* — Oblon, Spivak, McClelland, Maier & Neustadt, L.L.P.

(57) ABSTRACT

A method to change development of a plant or plant part, when compared to the wild-type plant or plant part, by increasing or decreasing expression in a plant or plant part of a cdc27a nucleic acid sequence and/or increasing or decreasing levels and/or activity in a plant of a CDC27A protein; a plant obtained by this method; a genetic construct for enacting the method; a food including the plant or plant part; an enzyme or pharmaceutical produced by the plant or plant part; and a method of making an enzyme or pharmaceutical by the plant or plant part.

25 Claims, 11 Drawing Sheets

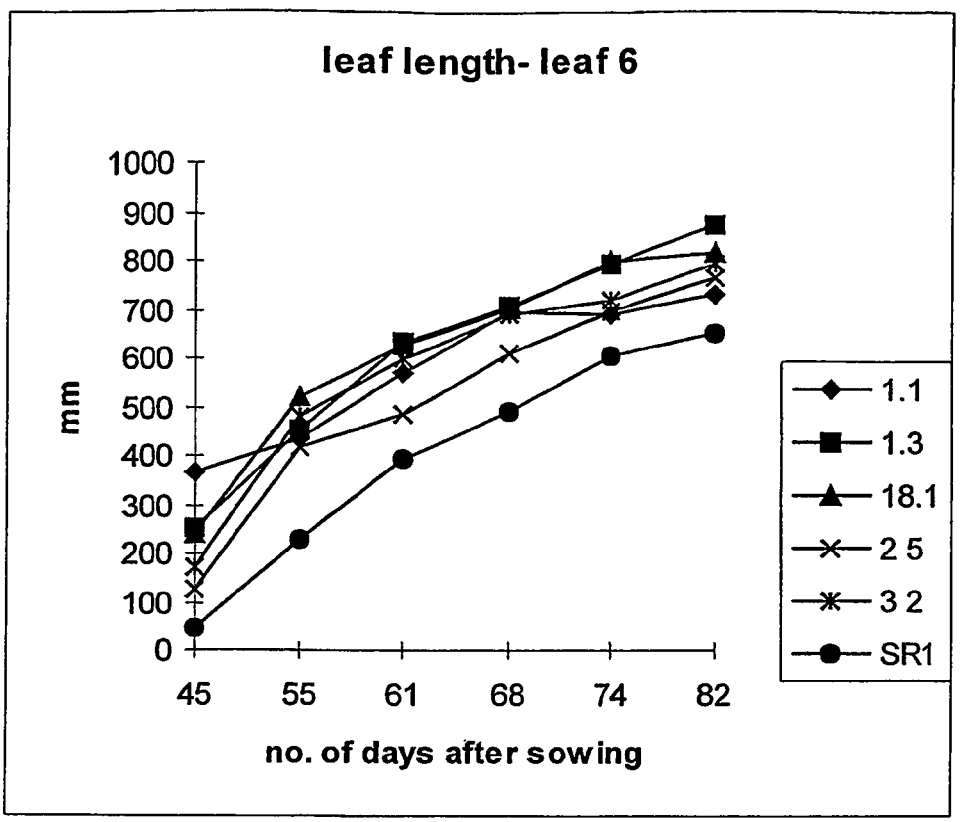
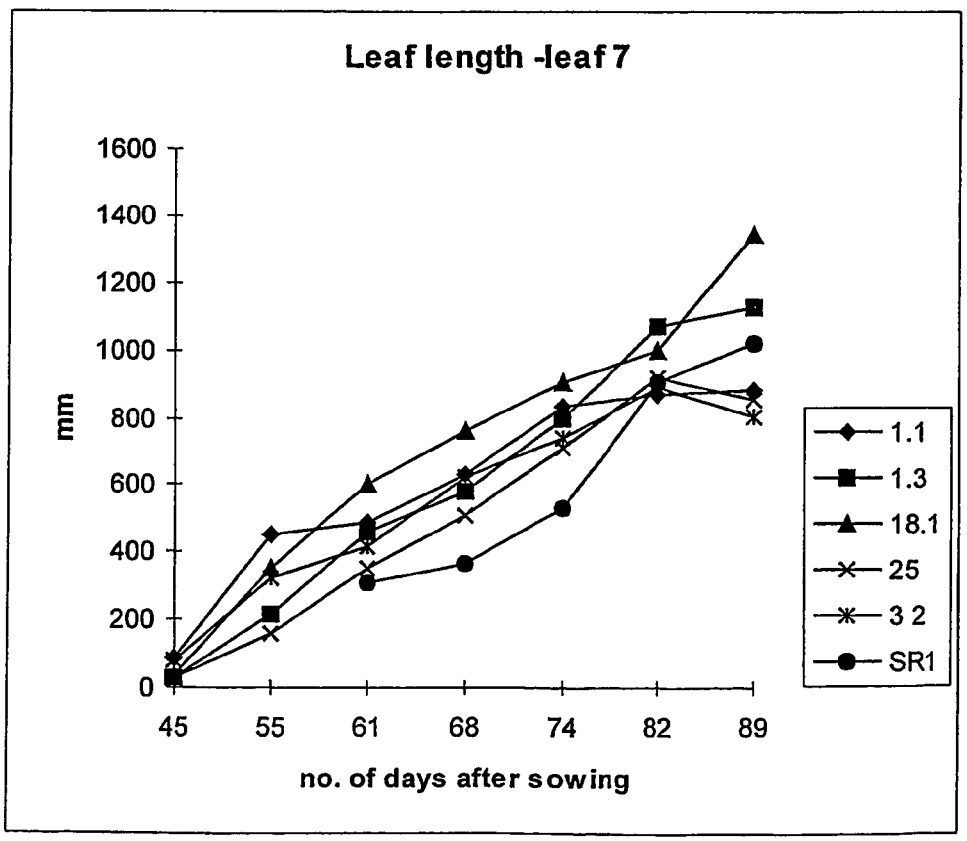
FIGURE 4

SEQ ID NO 1 cDNA Arabidopsis thaliana cdc27A1
ATGATGGAGAATCTACTGGCGAATTGTGTCCAGAAAAACCTTAACCATTTTATGTTCACCAA
TGCTATCTTCCTTTGCGAACTTCTTCTCGCCCAATTTCCATCTGAGGTGAACCTGCAATTGT
TAGCCAGGTGTTACTTGAGTAACAGTCAAGCTTATAGTGCATATTATATCCTTAAAGGTTCA
AAAACGCCTCAGTCTCGGTATTTATTTGCATTCTCATGCTTTAAGTTGGATCTTCTTGGAGA
GGCTGAAGCTGCATTGTTGCCCTGTGAAGATTATGCTGAAGAAGTTCCTGGTGGTGCAGCTG
GCATTATCTTCTTGGTCTTATATATAGATATTCTGGGAGGAAGAACTGTTCAATACAACAG
TTTAGGATGGCATTGTCATTTGATCCATTGTGTTGGGAAGCATATGGAGAACTTTGTAGTTT
AGGTGCCGCTGAAGAAGCCTCAACAGTTTTCGGGAATGTTGCTTCCCAGCGTCTTAAAACTT
GTGTAGAACAAAGAATAAGCTTCTCAGAAGGAGCAACCATAGACCAGATTACAGATTCTGAT
AAGGCCTTAAAAGATACAGGTTTATCGCAAACAGAACACATTCCAGGAGAGAACCAACAAGA
TCTGAAAATTATGCAGCAGCCTGGAGATATTCCACCAAATACTGACAGGCAACTTAGTACAA
ACGGATGGGACTTGAACACACCTTCTCCAGTGCTTTTACAGGTAATGGATGCTCCACCGCCT
CTGCTTCTTAAGAATATGCGTCGTCCAGCAGTGGAAGGATCTTTGATGTCTGTACATGGAGT
GCGTGTGCGTCGAAGAAACTTTTTTAGTGAAGAATTGTCAGCAGAGGCTCAAGAAGAATCTG
GGCGCCGCCGTAGTGCTAGAATAGCAGCAAGGAAAAAGAATCCTATGTCGCAGTCATTTGGA
AAAGATTCCCATTGGTTACATCTTTCACCTTCCGAGTCAAACTATGCACCTTCTCTTTCCTC
GATGATTGGAAAATGCAGAATCCAAAGCAGCAAGAAGCGATTCCTGATACCGTTACTCTAA
ATGATCCAGCAACGACGTCAGGCCAGTCTGTAAGTGACACTGGAAGCTCTGTTGATGATGAG
GAAAAGTCAAATCCTAGTGAATCTTCCCCGGATCGTTTCAGCCTTATTTCTGGAATTTCAGA
AGTGCTAGGCATTCTGAAAATTCTTGGAGATGGCCACAGGCATTTACATATGTACAAGTGTC
AGGAAGCTTTGTTGGCATATCAAAAGCTATCTCAGAAACAATACAATACACACTGGGTTCTC
ATGCAGGTTGGAAAAGCATATTTTGAGCTACAAGACTACTTCAACGCTGACTCTTCCTTTAC
TCTTGCTCATCAAAAGTATCCTTATGCTTTGGAAGGAATGGATACATACTCCACTGTTCTTT
ATCACCTGAAAGAAGAGATGAGGTTGGGCTATCTGGCTCAGGAACTGATTTCAGTTGATCGC
CTGTCTCCAGAATCCTGGTGTGCAGTTGGGAACTGTTACAGTTTGCGTAAGGATCATGATAC
TGCTCTCAAAATGTTTCAGAGAGCTATCCAACTGAATGAAAGATTCACATATGCACATACCC
TTTGTGGCCACGAGTTTGCCGCATTGGAAGAATTCGAGGATGCAGAGAGATGCTACCGGAAG
GCTCTGGGCATAGATACGAGACACTATAATGCATGGTACGGTCTTGGAATGACCTATCTTCG
TCAGGAGAAATTCGAGTTTGCGCAGCATCAATTTCAACTGGCTCTCCAAATAAATCCAAGAT
CTTCAGTCATCATGTGTTACTATGGAATTGCTTTGCATGAGTCAAAGAGAAACGATGAGGCG
TTGATGATGATGGAGAAGGCTGTACTCACTGATGCAAAGAATCCGCTCCCCAAGTACTACAA
GGCTCACATATTAACCAGCCTAGGTGATTATCACAAAGCACAGAAAGTTTTAGAAGAGCTCA
AAGAATGTGCTCCTCAAGAAAGCAGTGTCCATGCATCGCTTGGCAAAATATACAATCAGCTA
AAGCAATACGACAAAGCCGTGTTACATTTCGGCATTGCTTTGGATTTAAGCCCTTCTCCATC
TGATGCTGTCAAGATAAAGGCTTACATGGAGAGGTTGATACTACCAGACGAGCTGGTGACGG
AGGAAAATTTGTAGATTTATTGTGCAGGTAATACACCAGATTATGTTTCTCATATAACCCAA
AGTCATCTGTAATTTTTCTCATCTTTAGATCAGTCTTGTGGACTAACCCTAAAACAAACTG
ATTATATAAACTTAGAGGGTAATATTACAGAAATTGTATAGAGTTGGGTTTGAATTTTCAT
TTCTTTTCCAAGTTGGAACTTTTGTTCAAAAAAAAAAAAAAAAAAAAAAAAAAAAAAAAAAA
AAAAAAAAAAAAAAAA

FIGURE 6

SEQ ID NO 2 protein Arabidopsis thaliana cdc27A1
MMENLLANCVQKNLNHFMFTNAIFLCELLLAQFPSEVNLQLLARCYLSNSQAYSAYYILKGS
KTPQSRYLFAFSCFKLDLLGEAEAALLPCEDYAEEVPGGAAGHYLLGLIYRYSGRKNCSIQQ
FRMALSFDPLCWEAYGELCSLGAAEEASTVFGNVASQRLQKTCVEQRISFSEGATIDQITDS
DKALKDTGLSQTEHIPGENQQDLKIMQQPGDIPPNTDRQLSTNGWDLNTPSPVLLQVMDALP
PLLLKNMRRPAVEGSLMSVHGVRVRRRNFFSEELSAEAQEESGRRRSARIAARKKNPMSQSF
GKDSHWLHLSPSESNYAPSLSSMIGKCRIQSSKEVIPDTVTLNDPATTSGQSVSDIGSSVDD
EEKSNPSESSPDRFSLISGISEVLSLLKILGDGHRHLHMYKCQEALLAYQKLSQKQYNTHWV
LMQVGKAYFELQDYFNADSSFTLAHQKYPYALEGMDTYSTVLYHLKEEMRLGYLAQELISVD
RLSPESWCAVGNCYSLRKDHDTALKMFQRAIQLNERFTYAHTLCGHEFAALEEFEDAERCYR
KALGIDTRHYNAWYGLMTYLRQEKFEFAQHQFQLALQINPRSSVIMCYYGIALHESKRNDE
ALMMMEKAVLTDAKNPLPKYYKAHILTSLGDYHKAQKVLEELKECAPQESSVHASLGKIYNQ
LKQYDKAVLHFGIALDLSPSPSDAVKIKAYMERLILPDELVTEENL

SEQ ID NO 3 Arabidopsis thaliana CDC27A2 cDNA
atgatggagaatctactggcgaattgtgtccagaaaaaccttaaccatttTatgttcaccaa
tgctatcttcctttgcgaacttcttctcgcccaatttccatctgaggtgaacctgcaattgt
tagccaggtgttacttgagtaacagtcaagcttatagtgcatattatatccttaaaggttca
aaaacgcctcagtctcggtatttatttgcattctcatgctttaagttggatcttcttggaga
ggctgaagctgcattgttgccctgtgaagattatgctgaagaagttcctggtggtgcagctg
gcattatcttcttggtcttatatatagatattctgggaggaagaactgttcaatacaacag
tttaggatggcattgtcatttgatccattgtgttgggaagcatatggagaactttgtagttt
aggtgccgctgaagaagcctcaacagttttcgggaatgttgcttcccagcgtcttaaaactt
gtgtagaacaaagaataagcttctcagaaggagcaaccatagaccagattacagattctgat
aaggccttaaaagatacaggtttatcgcaaacagaacacattccaggagagaaccaacaaga
tctgaaaattatgcagcagcctggagatattccaccaaatactgacaggcaacttagtacaa
acggatgggacttgaacacaccttctccagtgcttttacaggtaatggatgctccaccgcct
ctgcttcttaagaatatgcgtcgtccagcagtggaaggatctttgatgtctgtacatggagt
gcgtgtgcgtcgaagaaaacttttttagtgaagaattgtcagcagaggctcaagaagaatctg
ggcgccgccgtagtgctagaatagcagcaaggaaaaagaatcctatgtcgcagtcatttgga
aaagattcccattggttacatctttcaccttccgagtcaaactatgcaccttctcttTcctc
gatgattggaaaatgcagaatccaaagcagcaagaagcaacgacgtcaggccagtctgtaa
gtgacactggaagctctgttgatgatgaggaaaagtcaaatcctagtgaatcttccccggat
cgtttcagccttatttctggaatttcagaagtgctaagcattctgaaaattcttggagatgg
ccacaggcatttacatatgtacaagtgtcaggaagctttgttggcatatcaaaagctatctc
agaaacaatacaatacacactgggttctcatgcaggttggaaaagcatattttgagctacaa
gactacttcaacgctgactcttcctttactcttgctcatcaaaagtatccttatgctttgga
aggaatggatacatactccactgttctttatacctgaaagaagagatgaggttgggctatc
tggctcaggaactgatttcagttgatcgcctgtctccagaatcctggtgtgcagttgggaac
tgttacagtttgcgtaaggatcatgatactgctctcaaaatgtttcagagagctatccaact
gaatgaaagattcacatatgcacataccctttgtggccacgagtttgccgcattggaagaat
cgaggatgcagagagatgctaccggaaggctctgggcatagatacgagacactataatgca
tggtacggtcttggaatgacctatcttcgtcaggagaaattcgagtttgcgcagcatcaatt
tcaactggctctccaaataaatccaagatcttcagtcatcatgtgttactatggaattgctt
tgcatgagtcaaagagaaacgatgaggcgttgatgatgatggagaaggctgtactcactgat
gcaaagaatccgctccccaagtactacaaggctcacatattaaccagcctaggtgattatca
caaagcacagaaagttttagaagagctcaagaatgtgctcctcaagaaagcagtgtccatg FIGURE 6 (continued)

```
catcgcttggcaaaatatacaatcagctaaagcaatacgacaaagccgtgttacatttcggc
attgctttggatttaagcccttctccatctgatgctgtcaagataaaggcttacatggagag
gttgatactaccagacgagctggtgacggaggaaaatttgtagatttattgtgcaggtaata
caccagattatgtttctcatataacccaaagtcatctgtaattttctcatctttagatcag
tcttgtggactaaccctaaaacaaaactgattatataaacttagagggtaatattacagaaa
attgtatagagttgggtttgaattttcatttcttttccaagttggaacttttgttcaaaaaa
aaaaaaaaaaaaaaaaaaaaaaaaaaaaaaaaaaaaaaaaaa
```

SEQ ID NO 4 Arabidopsis thaliana CDC27A2 protein
```
MMENLLANCVQKNLNHFMFTNAIFLCELLLAQFPSEVNLQLLARCYLSNSQAYSAYYILKGS
KTPQSRYLFAFSCFKLDLLGEAEAALLPCEDYAEEVPGGAAGHYLLGLIYRYSGRKNCSIQQ
FRMALSFDPLCWEAYGELCSLGAAEEASTVFGNVASQRLKTCVEQRISFSEGATIDQITDSD
KALKDTGLSQTEHIPGENQQDLKIMQQPGDIPPNTDRQLSTNGWDLNTPSPVLLQVMDAPPP
LLLKNMRRPAVEGSLMSVHGVRVRRRNFFSEELSAEAQEESGRRRSARIAARKKNPMSQSFG
KDSHWLHLSPSESNYAPSLSSMIGKCRIQSSKEATTSGQSVSDTGSSVDDEEKSNPSESSPD
RFSLISGISEVLSILKILGDGHRHLHMYKCQEALLAYQKLSQKQYNTHWVLMQVGKAYFELQ
DYFNADSSFTLAHQKYPYALEGMDTYSTVLYHLKEEMRLGYLAQELISVDRLSPESWCAVGN
CYSLRKDHDTALKMFQRAIQLNERFTYAHTLCGHEFAALEEFEDAERCYRKALGIDTRHYNA
WYGLGMTYLRQEKFEFAQHQFQLALQINPRSSVIMCYYGIALHESKRNDEALMMMEKAVLTD
AKNPLPKYYKAHILTSLGDYHKAQKVLEELKECAPQESSVHASLGKIYNQLKQYDKAVLHFG
IALDLSPSPSDAVKIKAYMERLILPDELVTEENL
```

SEQ ID NO 5 Oryza sativa CDC27 cDNA partial
```
atggaaaccctaatggtggaccgcgtccacggcagcctccgcctcttcatgcaccgcaacgc
cgtcttcctctgcgagcgcctctgcgccagttccccgccgagacaaatgtccagttgctag
caacttgctaccttcacaacaaccagccatatgctgcataccacatcttgaaaggaaagaag
ctgccagagtcccggtacttgtttgctatgtcatgcttccgaatgaacctcttacgggaagc
tgaagaagccttgtgtcctgtcaatgaaccaaatattgaggttccaagtggtgcaacagggc
actaccttcttggagtaatttacaggtacactggcagagtggaagctgcagctgagcaattt
gtacaagctctgactcttgatcctcttctatgggcagcatacgaggaattgtgcatactagg
tgttgctgaagatgcaaatgaatgtttcagtgaagcaacagctctacgtcttcagcaggaac
tcacatccacatcaaatgtggaaaagtcaaactttgttaatgaaatcggtttctatcttcc
aatgtgtcagcaagttttggtgatagtcctaagcaaattaaacagctgcatgctaacaccac
tgcagaagtatctggttatcctcatgtaaagtcaactgcattgcatatgcagaacggtgcac
catctaatttatcacagtttgacactccatcgccaacttcaacgcagnnnnataatgtaact
tcaacttcgtcttctacaagtatagttgatggaagatatcccgagcaagagaaatctgaacg
agttctgtcacaggactccaaattagctattggtatcagggagctaatggcactcttgcgga
cactaggggaagggtataggctttcttgcttgtttaagtgtcaggaagcattggaagtatat
agaaagctcccagaggcacaatttaatactggatggttctttgccaggttgggaagacata
ttttgaactcgtcaattatttagaagccgatcatttttttgagttagcgcatcgactatcac
catgcacgttggagggaatggacatttactccactgttctttatcatttgaatgaggaaatg
cggctaagttaccttgctcaagatcttgtttctattgatcgactatctccccaagcatggtg
tgctgtgggaaattgctttgccttgaggaaagatcatgagactgccttgaagaattttcaac
gtgctgtacagcttgactcaagagttgcatacgctcacacgctatgcggtcacgatataaaa
ctataccgatctgcacttcaggtagatgaaagacactacaatgcctggtatggccttggagt
ggtgtaccttcgccaggaaaagtttgagtttgctgagcatcatttcagaagggcattccaga
```

```
taaatccttgctcttctgttcttatgtgctatcttgggatggccttgcatgctttaaagagg
aatgaggaagccttggaaatgatggagaaggctatatttgctgataagaagaatccactccc
caagtatcaaaaggctttaatccttctaggcctacaaaaatacccctgatgctctggatgagt
tggaacggctaaaggaaattgcacctcatgaaagtagtatgtatgcactgatgggaaagatt
tacaagcaacttaacattcttgacaaggctgtattttgctttggcattgccctggatttgaa
acctcctgctgctgacgttgctataatacaatctgcaatggagaaagtacaccttccagatg
aacttatggatgatgatgatgatgatgatgagatttaagctcactccgaagaacagaggga
ggaaccaacattgattggcatgcctgtgcttg
```

SEQ ID NO 6 Oryza sativa CDC27 protein partial
METLMVDRVHGSLRLFMHRNAVFLCERLCAQFPAETNVQLLATCYLHNNQPYAAYHILKGKK
LPESRYLFAMSCFRMNLLREAEEALCPVNEPNIEVPSGATGHYLLGVIYRYTGRVEAAAEQF
VQALTLDPLLWAAYEELCILGVAEDANECFSEATALRLQQELTSTSNVEKSNFVNENRFLSS
NVSASFGDSPKQIKQLHANTTAEVSGYPHVKSTALHMQNGAPSNLSQFDTPSPTSTQXXNVT
STSSSTSIVDGRYPEQEKSERVLSQDSKLAIGIRELMALLRTLGEGYRLSCLFKCQEALEVY
RKLPEAQFNTGWVLCQVGKTYFELVNYLEADHFFELAHRLSPCTLEGMDIYSTVLYHLNEEM
RLSYLAQDLVSIDRLSPQAWCAVGNCFALRKDHETALKNFQRAVQLDSRVAYAHTLCGHDIK
LYRSALQVDERHYNAWYGLGVVYLRQEKFEFAEHHFRRAFQINPCSSVLMCYLGMALHALKR
NEEALEMMEKAIFADKKNPLPKYQKALILLGLQKYPDALDELERLKEIAPHESSMYALMGKI
YKQLNILDKAVFCFGIALDLKPPAADVAIIQSAMEKVHLPDELMDDDDDDEI

SEQ ID NO 7 Saccharum sp. CDC27 partial nucleotide sequence
```
ggtcgacccacgcgtccgaccggaccctcccactgctgcgcctgccgcctgcgcttcggcca
ccgcacaacacttcccctcgctctcgcccgcccgcccgcgctcgccgccgccgccgccgccg
ggcggagatggaaaccctaatggtggaccgcgtccacagcagcctccgcctcttcatgcacc
gcaacgccgtattcctctgcgagcgcctctgcgcgcagttcccctccgagaccaatgtgcaa
ttgttagcgacctgctacctccacaacaatcagccatatgctgcataccacattttgaaagg
gaagaagctgccggagtcccggtacttgtttgctacatcatgctttcgaatgaacctcttgc
gtgaagcagaagaaactctatgtccagtcaatgaaccaaacatggaggttccaagtggagca
acaggacactacctccttggagtgatttacaggtgcacaggcagaatttcagctgcagctga
acaatttacacaagcgttgactctagatcctctttttatgggcggcatatgaggaattgtgta
tattaggtattgctgaagatactgatgagtgttttagtgaatcgactgctctacgtctccag
caggaacacacatccacggccactctggtgaagtcgaacttcgccaatgaaaatcgagttct
atcatccagggtctctgcaaatcttggggatattagtcctaagcaaatcaaacagcttcatg
ctaacaacatagcagaagtatctggctatcctcatgtaagaccaactgcattgcatgtgcag
aacagttcaacctctaatgtagcacagtttgacacccatcaccaactgcagcacagacttc
tagtatcatgccaccaccactctttaggaatgtccatgcttanattcaaattcaaatacctg
gggtttggagggaatggtacaggttattcgtcagggaaattgcgagtaaactcgtccacacc
atcaaaatggtgttaaccaccatacgttccgtgcaagttaggaaaggaaaaccacgggctac
agaaaattttgatgaaggaagtagatatgaagtcattgatgaaatgtggacagacaatatat
caggaacttcatcttctgtaagtacagctgatggaagatcctttgagcaagataaagctgaa
cgaattctgttgcaagactccaaattggcacttggtattagggagatattgggacttgtccg
aacactcggtgaaggttgtaggctttcttgcttgtttaagtgccatgaagccttggaagtct
acagaagactccctgagacccattntagcactggatggagcatatgccaggttggtaaggca
tatttcgaattagttgattatttggaagctgatcgttactttgaattggcacaccgactgtc
```

FIGURE 6 (continued)

```
gccttgtacgcttgatggaatggacatctattctactgttctttatcatctgaatgaggaaa
tgagactaagctaccttgctcaagagcttatttccattgatcgactatctcctcaagcatgg
tgtgcagtgggcaattgctttgccttgaggaaagatcatgagactgctttgaagaattttca
acgttcggtacagcttgactcaagatttgcatatgctcacactctatgtggtcatgagtatt
ctgcattggaggattatgagaatagtatcaaattctaccggtgtgcactgcaggtagatgaa
aggcactacaatgcctggtatggccttggggtggtgtatcttcgccaggaaaagtntgagtt
tgctgagcatcatttcagaagggcatttcagataaatcctcgctcttctgttctcatgtgct
atcttgggatggcgttgcattctcttaagaggaaggaggaggcattggaaatgatggagaaa
gctatagcagctgataagaagaatccactgcccaagtatcagaaggccttaatccttctagg
tcttcagaagtatcaagaagctctggatgagttggagcggctaaaggagattgcacctcatg
agagcagtatgtatgcactgatgggaaagatttacaagcaactcaatatccttgacaaagct
gttttctgctttggcattgccctggatttgaaacctcctgctgctgatcttgctataattaa
gtccgcaatggagaaagtacatctccctgatgaactgatggaggatgacctgtaagttcgct
caagcacagtgagaaggaacatttacttcgggtccatgatgctttgcttgtgcttcgtgtt
cctggcctgcttaggcttctcaagtggaactcagatcttggagctgtaccatcaaccatcca
gttttgtagatttagttgtagcctataatcagagaacacatgcgcagaagctgcagtagttt
aggactctgtacaagttgagcgttggcaaaatgacgcctgtaccattatacagttgtgatat
taacaaaacacatccttgtcaaataacggaaataatcaaaggatgaggatcctgctgattca
agcagattgtttgtcgc
```

SEQ ID NO 8 Saccharum sp. CDC27 partial protein sequence
METLMVDRVHSSLRLFMHRNAVFLCERLCAQFPSETNVQLLATCYLHNNQPYAAYHILKGKK
LPESRYLFATSCFRMNLLREAEETLCPVNEPNMEVPSGATGHYLLGVIYRCTGRISAAAEQF
TQALTLDPLLWAAYEELCILGIAEDTDECFSESTALRLQQEHTSTATLVKSNFANENRVLSS
RVSANLGDISPKQIKQLHANNIAEVSGYPHVRPTALHVQNSSTSNVAQFDTPSPTAAQTSSI
MPPPLFRNVHAXIQIQIPGVWREWYRLFVREIASKLVHTIKMVLTTIRSVQVRKGKPRATEN
FDEGSRYEVIDEMWTDNISGTSSSVSTADGRSFEQDKAERILLQDSKLALGIREILGLVRTL
GEGCRLSCLFKCHEALEVYRRLPETHXSTGWSICQVGKAYFELVDYLEADRYFELAHRLSPC
TLDGMDIYSTVLYHLNEEMRLSYLAQELISIDRLSPQAWCAVGNCFALRKDHETALKNFQRS
VQLDSRFAYAHTLCGHEYSALEDYENSIKFYRCALQVDERHYNAWYGLGVVYLRQEKXEFAE
HHFRRAFQINPRSSVLMCYLGMALHSLKRKEEALEMMEKAIAADKKNPLPKYQKALILLGLQ
KYQEALDELERLKEIAPHESSMYALMGKIYKQLNILDKAVFCFGIALDLKPPAADLAIIKSA
MEKVHLPDELMEDDL*

SEQ ID NO 9 Zea mays EST nucleotide
ACAGCTTGACTCAAGATTTGCATATGCTCACACTCTATGTGGTCATGAGTATTCTGCACTGG
AGGATTATGAGAATAGTATCAAATTCTACAGATGTGCACTGCAGGTAGATGAAAGGCACTAC
AATGCTTGGTATGGCCTTGGGGTGGTGTATCTTCGCCAGGAAAAGTTTGAGTTTGCTGAGCA
TCATTTCAGAAGGGCATTTCAGATAAATCCTCGCTCTTCTGTTCTCATGTGCTATCTTGGGA
TGGCCTTGCATTCTCTTAAGAGGAATGAAGAGGCACTGGAAATGATGGAGAAAGCTATAGCA
GCTGATAAGAAGAATCCACTGCCCAAGTATCAGAAGTCCTTAATTCTTCTAGGACTAATGAA
GTATGAAGAAGCTCTGGATGAGTTGGAGCGGCTAAAGGAGATTGCACCTCATGAGAGTAGTA
TGTATGCACTGATGGGAAAGATTTACAAGCAACTCAATATTCTTGACAAAGCTGTTTTCTGC
TTCGGCATTGCCCTGGATTTGAAACCACCTGCTGCTGATCTTGCTATAATTAAGTCCGCAAT
GGAGAAAGTACCTCGGCCGCGACCACGC FIGURE 6 (continued)

SEQ ID NO 10 protein translation of Zea Mays EST
QLDSRFAYAHTLCGHEYSALEDYENSIKFYRCALQVDERHYNAWYGLGVVYLRQEKFEFAEH
HFRRAFQINPRSSVLMCYLGMALHSLKRNEEALEMMEKAIAADKKNPLPKYQKSLILLGLMK
YEEALDELERLKEIAPHESSMYALMGKIYKQLNILDKAVFCFGIALDLKPPAADLAIIKSAM
EKVPRP

SEQ ID NO 11 Sorghum bicolor EST BF657465 nucleotide:
CTCCACAACAATCAGCCATATGCTGCATACCACATTTTGAAAGGGAAGAAGATGCCGGAGTC
CCGGTACTTGTTTGCTACATCATGTTTTCGAATGAACCTCTTGCGTGAAGCAGAAGAAACTC
TATGTCCAGTCAATGAACCAAACATGGAGGTTCCAAGTGGAGCAACAGGACACTACCTCCTT
GGAGTGATTTACAGGTGCACAGGCAGAATTTCAGCTGCAGCTGAACAATTTACACAAGCGTT
GACTCTAGATCCTCTTTTATGGGCGGCATATGAGGAATTGTGTATATTAGGTATTGCTGAAG
ATACCGATGAGTGTTTTAGTGAATCGACTGCTCT

SEQ ID NO 12 protein translation of Sorghum bicolor EST BF657465
LHNNQPYAAYHILKGKKMPESRYLFATSCFRMNLLREAEETLCPVNEPNMEVPSGATGHYLL
GVIYRCTGRISAAAEQFTQALTLDPLLWAAYEELCILGIAEDTDECFSESTA

SEQ ID NO 13 Triticum aestivum EST CD904062 nucleotide
ACCCACGCGTCCGCACGAATATTCTNGCATTGGAGGATTACGAGAACAGTGTTAAATTCTAC
CGATGTGCACTTCAGGTAGATGAAAGGCACTACAATGCCTGGTATGGGCTTGGAGTAGTTTA
CCTTCGCCAGGAAAAGTTTGAGTTTGCTGAGCATCATTTTAGAAGGGCATTTCAGATAAATC
CCCGCTCTTCTGTTCTTATGTGCTATCTTGGGATGGCCTTACATGCTCTAAAGAGAGATGAG
GATGCATTGGAGATGATGGAGAAAGCCATATTTTCTGATAAGAAGAATCCACTTCCTAAGTA
TCAGAAGGCTTTAATTCTGGTAGGCCTTCAAAAATATCAGGAGGCTCTGGATGAGTTGGAAC
GGCTAAGGGAGATTGCACCTCATGAGAGTAGTATGTATGCACTTATGGGCAAGATATACAAG
CAACTCAATATTCTCGACAAGGCTGTATTTTGCTTTGGCGTTGCCCTTGATTTGAAACCTCC
CGCTGCCGACCTTGCTATAATCAAGTCTGCAATGGAGAAAGTACACCTTCCAGATGAACTGA
TGGAGGATGATGACCTGTAAGTTCACTTTAAAGCACAAACTGAGAAATGGACATTTATTCAG
ATCTATGAGTTTCTGCTTGTGCTTCCGAGTCATGGCCTGAATGTGCTTTCGGAGAGGAACTC
AGAGGTTGAAGGAAGCAAGCACATCATGCGGAA

SEQ ID NO 14 Protein translation of Triticum aestivum EST CD904062
ALEDYENSVKFYRCALQVDERHYNAWYGLGVVYLRQEKFEFAEHHFRRAFQINPRSSVLMCY
LGMALHALKRDEDALEMMEKAIFSDKKNPLPKYQKALILVGLQKYQEALDELERLREIAPHE
SSMYALMGKIYKQLNILDKAVFCFGVALDLKPPAADLAIIKSAMEKVHLPDELMEDD

FIGURE 6 (continued)

PLANTS HAVING CHANGED DEVELOPMENT AND A METHOD FOR MAKING THE SAME

CROSS REFERENCES TO RELATED APPLICATIONS

This application is a national stage application of International Patent Application No. PCT/EP03/10087, filed on Sep. 5, 2003, and claims priority to International Patent Application No. PCT/EP02/10265, filed on Sep. 5, 2002, both of which are incorporated herein by reference in their entireties.

The present invention concerns a method for changing development of a plant. More specifically, the present invention concerns a method for changing plant development by increased or decreased expression of a cdc27a nucleic acid and/or by increased or decreased activity and/or levels of a CDC27A protein in a plant. The present invention also concerns plants having increased or decreased expression of a cdc27a nucleic acid and/or increased or decreased activity and/or levels of a CDC27A protein, which plants have changed development relative to corresponding wild type plants.

The ever-increasing world population and the dwindling supply of arable land available for agriculture fuel agricultural research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Crop yield is influenced by the typical stresses to which plants or crops are subjected. Such stresses include environmental (abiotic) stresses (such as temperature stresses caused by atypical high or low temperatures; stresses caused by nutrient deficiency; stresses caused by lack of water (drought)) and biotic stresses (which can be imposed on plants by other plants (weeds), animal pests and pathogens). Crop yield may not only be increased by combating one or more of the stresses to which the crop or plant is subjected, but may also be increased by modifying the inherent growth and development mechanisms of a plant.

The inherent growth mechanisms of a plant reside in a highly ordered sequence of events collectively known as the 'cell cycle'. Progression through the cell cycle is fundamental to the growth of the organisms and is crucial to cell proliferation. The major components of the cell cycle are highly conserved in yeast, mammals and plants. The cell cycle is typically divided into the following sequential phases: G0-G1-S-G2-M. DNA replication or synthesis generally takes place during the S phase ("S" is for DNA synthesis) and mitotic segregation of the chromosomes occurs during the M phase (the "M" is for mitosis), with intervening gap phases, G1 (during which cells grow before DNA replication) and G2 (a period after DNA replication during which the cell prepares for division). Cell division is completed after cytokinesis, the last step of the M phase. Cells that have exited the cell cycle and that have become quiescent are said to be in the G0 phase. Cells in this phase can be stimulated to re-enter the cell cycle at the G1 phase. The "G" in G1, G2 and G0 stands for "gap". Completion of the cell cycle process allows each daughter cell during cell division to receive a full copy of the parental genome.

Cell division is controlled by two principal cell cycle events, namely initiation of DNA synthesis and initiation of mitosis. Each transition to each of these key events is controlled by a checkpoint represented by specific protein complexes (involved in DNA replication and division). The transition between the different phases of the cell cycle, and therefore progression through the cell cycle, is driven by the formation and activation of different heterodimeric serine/threonine protein kinases, generally referred to as cyclin-dependent kinases (CDKs). Progression trough the cell cycle involves alternating phases of high and low activity of cyclin-dependent kinases. The anaphase-promoting complex (APC) is a multisubunit ubiquitin ligase triggering proteolytic destruction of mitotic cyclins and is an important regulator of the low-activity phase of cyclin dependent kinases. Cdc27 has been described as a member of the APC complex, which is involved in the degradation of mitotic cyclins during of the cell cycle to promote the anaphase of mitosis.

The inherent development mechanisms of a plant reside in sequence of events leading to cell differentiation, which is crucial for the function of a multicellular organism. The meristem regions of higher plants contain cells with high mitotic activity and these regions continuously produce new cells. Once departed from the meristem, the cells expand and fully differentiate. This differentiation continues when mitotic activity ceases, so that plant development can proceed.

The ability to influence the differentiation and development in a plant (either using recombinant DNA technology or using non-recombinant means), and to thereby modify various developmental characteristics of a plant, would have many applications in areas such as crop enhancement, plant breeding, production of ornamental plants, aboriculture, horticulture and forestry.

The isolation and characterization of a cdc27a gene from *Arabidopsis thaliana* was described in international patent application WO0102430. In WO0102430 there is disclosed the use of cdc27a muteins or the down-regulation of cdc27 to cause a malfunction of the APC complex and to cause endoreduplication via stimulation of DNA synthesis and/or blockage of mitosis. This document describes the link between cdc27A and DNA synthesis and/or mitosis and the use of cdc27a genes, proteins or inactivated variants/muteins in a plants, to influence processes involving DNA synthesis and/or mitosis such as DNA replication, cell division and endoreduplication.

It has now been found that increasing or decreasing expression in a plant of a cdc27a nucleic acid and/or increasing or decreasing activity and/or levels in a plant of a CDC27A protein gives plants having accelerated development. Since plant differentiation and development are processes occurring after DNA synthesis and cell division, it was surprising to find that these processes were influenced by the cdc27a transgene. More particularly, the effects of the cdc27a transgene were accelerated rate of development, increased of size and/or number of organs and early flowering, which processes are based on differentiation of the cells and developmental patterns rather than on DNA synthesis and cell division.

Therefore according to a first embodiment of the present invention, there is provided a method to change development of a plant or plant part compared to the wild-type plant or plant part, which method comprises increasing or decreasing expression in a plant of a cdc27a nucleic acid sequence and/or increasing or decreasing levels and/or activity in a plant of a CDC27A protein.

Increasing or decreasing expression of a cdc27a nucleic acid and/or increasing or decreasing of the activity and/or levels of a CDC27A protein encompasses changed expression of a gene and/or changed activity and/or levels of a gene product, namely a polypeptide, in specific cells or tissues. The changed expression, activity and/or levels is changed compared to expression, activity and/or levels of a cdc27a gene or protein in corresponding wild-type plants. The changed gene expression may result from changed expression levels of an endogenous cdc27a gene and/or may result from changed expression levels of a cdc27a gene previously introduced into a plant. Similarly, changed levels and/or activity of a CDC27A protein may be due to changed expression of an endogenous cdc27a nucleic acid/gene and/or due to changed expression of a cdc27a nucleic acid/gene previously introduced into a plant. Increasing or decreasing expression of a gene/nucleic acid and/or increasing or decreasing activity and/or levels of a gene product may be effected, for example, by chemical means and/or recombinant means.

Advantageously, increase or decrease of expression of a cdc27a nucleic acid and/or increase or decrease of activity and/or levels of a CDC27A protein may be effected by chemical means, i.e. by exogenous application of one or more compounds or elements capable of increasing or decreasing activity and/or levels of the CDC27A protein and/or capable of increasing or decreasing expression of a cdc27a nucleic acid/gene. The term "exogenous application" as defined herein is taken to mean the contacting or administering of a suitable compound or element to plant cells, tissues, organs or to the whole organism. The compound or element may be exogenously applied to a plant in a form suitable for plant uptake (such as through application to the soil for uptake via the roots, or in the case of some plants by applying directly to the leaves, for example by spraying). The exogenous application may take place on wild-type plants or on transgenic plants that have previously been transformed with a cdc27a nucleic acid/gene or another transgene.

Suitable compounds or elements include CDC27A proteins or cdc27a nucleic acids. Similarly, homologues, derivatives or active fragments of CDC27A proteins and/or portions or sequences capable of hybridizing with a cdc27a nucleic acid may also be used. The exogenous application of compounds or elements capable of increasing or decreasing levels of factors that directly or indirectly activate or inactivate a CDC27A protein will also be suitable in practising the invention. Also included are antibodies that can recognise or mimic the function of cdc27A proteins. Such antibodies may comprise "plantibodies", single chain antibodies, IgG antibodies and heavy chain camel antibodies, as well as fragments thereof. Additionally or alternatively, the resultant effect may also be achieved by the exogenous application of an interacting protein or activator or an inhibitor of the cdc27a gene/gene product. Additionally or alternatively, the compound or element may be a mutagenic substance, such as a chemical selected from any one or more of: N-nitroso-N-ethylurea, ethylene imine, ethyl methanesulphonate and diethyl sulphate. Mutagenesis may also be achieved by exposure to ionising radiation, such as X-rays or gamma-rays or ultraviolet light. Methods for introducing mutations and for testing the effect of mutations (such as by monitoring gene expression and/or protein activity) are well known in the art.

Therefore, according to one aspect of the present invention, there is provided a method for changing development of a plant, comprising exogenous application of one or more compounds or elements capable of increasing or decreasing expression of a cdc27a gene and/or capable of increasing or decreasing activity and/or levels of a CDC27A protein.

Additionally or alternatively, and according to a preferred embodiment of the present invention, increase or decrease of expression of a cdc27a nucleic acid and/or increase or decrease of activity and/or levels of a CDC27A protein may be effected by recombinant means. Such recombinant means may comprise a direct and/or indirect approach for increase or decrease of expression of a nucleic acid and/or for increase or decrease of the activity and/or levels of a protein.

Therefore there is provided by the present invention, a method to change plant development, comprising increasing or decreasing cdc27a gene expression and/or CDC27A protein levels and/or CDC27A protein activity, which increase or decrease may be effected by recombinant means and/or by chemical means.

The cdc27a gene or the CDC27A protein in a plant may be wild type, i.e. a native or endogenous nucleic acid or polypeptide. Alternatively, it may be a nucleic acid derived from the same or another species, which gene is introduced as a transgene, for example by transformation. This transgene may be substantially changed from its native form in composition and/or genomic environment through deliberate human manipulation.

An indirect recombinant approach may comprise for example introducing, into a plant, a nucleic acid capable of increasing or decreasing activity and/or levels of the protein in question (a CDC27A protein) and/or capable of increasing or decreasing expression of the gene in question (a cdc27a gene). Examples of such nucleic acids to be introduced into a plant, are nucleic acids encoding transcription factors or activators or inhibitors that bind to the promoter of a cdc27a gene or that interact with a CDC27A protein. Methods to test these types of interactions and methods for isolating nucleic acids encoding such interactors include yeast one-hybrid or a yeast two-hybrid screens.

Also encompassed by an indirect approach for increasing or decreasing activity and/or levels of a CDC27A protein and/or expression of a cdc27a gene, is the provision of, or the inhibition or stimulation of regulatory sequences that drive expression of the native cdc27a gene or of the cdc27a transgene. Such regulatory sequences may be introduced into a plant. For example, the nucleic acid introduced into the plant is a promoter, capable of driving the expression of an endogenous cdc27a gene.

A further indirect approach for increasing or decreasing activity and/or levels and/or expression of a cdc27a gene or protein in a plant, encompasses increased or decreased levels in a plant of a factor able to interact with CDC27A. Such factors may include ligands of CDC27A. Therefore, the present invention provides a method for changing development of a plant, when compared to the corresponding wild-type plants, comprising increasing or decreasing expression of a gene coding for a protein which is a natural ligand of a CDC27A. Furthermore, the present invention also provides a method for changing development of a plant relative to corresponding wild-type plants, comprising increasing or decreasing expression of a gene coding for a protein which is a natural target/substrate of a CDC27A.

A direct and more preferred approach for changing development of a plant, comprises introducing into a plant a cdc27a nucleic acid, or a portion thereof or sequences capable of hybridising therewith, which nucleic acid preferably encodes a CDC27A protein or a homologue, derivative or active fragment thereof. The nucleic acid may be introduced into a plant by, for example, transformation.

According to one preferred aspect of the present invention, there is provided a method for changing plant development, a nucleic acid sequence capable of increasing or decreasing expression of a cdc27a gene and/or capable of increasing or decreasing activity and/or levels of a CDC27A protein. Further preferably such nucleic acid sequence is a cdc27a nucleic acid.

As mentioned above the nucleic acid to be used in the methods of the present invention can be wild type (native or endogenous). Alternatively, the nucleic acid may be derived from another species, which gene is introduced into the plant as a transgene, for example by transformation. The nucleic acid may thus be derived (either directly or indirectly (if subsequently modified)) from any source provided that the nucleic acid, when expressed in a plant, leads to increased or decreased expression of a cdc27a nucleic acid/gene or increased or decreased activity and/or levels of a CDC27A protein. The nucleic acid may be isolated from a microbial source, such as bacteria, yeast or fungi, or from a plant, algae, insect, or animal (including human) source. This nucleic acid may be substantially changed from its native form in composition and/or genomic environment through deliberate human manipulation. The nucleic acid sequence is preferably a homologous nucleic acid sequence, i.e. a nucleic acid sequence obtained from a plant, whether from the same plant species or different. The nucleic acid may be isolated from a *dicotyledonous* species, preferably from the family Brassicaceae, further preferably from *Arabidopsis thaliana*. More preferably, the nucleic acid is as represented by SEQ ID NO: 1 or a portion thereof or a nucleic acid capable of hybridising therewith or is a nucleic acid encoding an amino acid represented by SEQ ID NO: 2 or a homologue derivative or active fragment thereof, such as a homologue having at least 47%, 48%, 49, 50%, 55%, 60%, 65%, 70%, 75%, 80%, 85%, 90%, 95% 98%, 99% sequence identity with SEQ ID NO 2.

Although the invention has been exemplified with a cdc27a according to SEQ ID NO: 1, and corresponding amino acids according to SEQ ID NO: 2, it would be apparent to a person skilled in the art that the methods according to the invention may also be practised using variant nucleic acids and variant amino acids, such as the ones defined hereinafter.

Therefore, taken in a broad context, the term "cdc27a" protein/nucleic acid also encompasses variant nucleic acids and variant amino acids suitable for practicing the methods according to the invention. Preferably, variant nucleic acids and variant amino acids suitable for practicing the methods according to the invention include those falling within the definition of a "cdc27a", meaning that upon construction of a phylogenetic tree, such as the one depicted in FIG. 7, the variant sequences of interest would tend to cluster around cdc27a proteins/genes. Further preferred cdc27a variants cluster around the cdc27a protein of *Arabidopsis* rather than around the cdc27b protein of *Arabidopsis*. In case of variants of particular plants for which no distinction between cdc27A or cdc27B can be made, preferred variants may cluster around a separate group of cdc27 proteins each of which may represent a unique cdc27 protein in the genome of said plant. Examples of such cdc27 proteins are monocots cdc27 proteins such as represented by SEQ ID NO 6 (rice), SEQ ID NO 8 (sugar cane), SEQ ID NO 10 (maize) and SEQ ID NO 12 (wheat). These cdc27 proteins are also useful for the methods of the present invention. Such a phylogenetic tree can be construed with amino acid sequences or with nucleic acid sequences. A person skilled in the art could readily determine whether any nucleic acid sequence or protein sequence in question falls within the definition of a "cdc27a" using known techniques and software for the making of such phylogenetic trees, such as a GCG, EBI or CLUSTAL package, or Align X, using default parameters. Upon construction of such a phylogenetic tree, sequences clustering in the cdc27a group will be considered to fall within the definition of a "cdc27a" as used herein and will therefore be useful in performing the methods of the invention.

Suitable variant nucleic acid and amino acid sequences useful in practising the method according to the invention, include:
(i) Functional portions of a cdc27a nucleic acid/gene;
(ii) Sequences capable of hybridising with a cdc27a nucleic acid/gene;
(iii) Alternative splice variants of a cdc27a nucleic acid/gene;
(iv) Allelic variants of a cdc27a nucleic acid/gene;
(v) Homologues, derivatives and active fragments of a cdc27a protein;

The term cdc27a nucleic acid/gene, as defined herein, also encompasses a complement of SEQ ID NO 1 and also to corresponding RNA, DNA, cDNA or genomic DNA. The cdc27a may be synthesized in whole or in part, it may be double-strand nucleic acid or single-stranded nucleic acid. Also this term encompasses a variant of the gene due to the degeneracy of the genetic code and variants that are interrupted by one or more intervening sequences.

An example of a variant cdc27a nucleic acid/gene is a functional portion of a cdc27a nucleic acid/gene. The methods according to the invention may advantageously be practised using functional portions of a cdc27a. A functional portion refers to a piece of DNA derived or prepared from an original (larger) DNA molecule, which DNA portion, when introduced and expressed in a plant, gives plants having changed development. The portion may comprise many genes, with or without additional control elements or may contain spacer sequences. The portion may be made by making one or more deletions and/or truncations to the nucleic acid sequence. Techniques for introducing truncations and deletions into a nucleic acid are well known in the art. Portions suitable for use in the methods according to the invention may readily be determined using routine techniques, such as by assaying for CDC27A activity and/or by following the methods described in the Examples section by simply substituting the sequence used in the actual Example with the portion to be tested for functionality.

Methods for assaying the activity of a CDC27A protein may comprise
1. Optionally, a first step of expressing the CDC27A encoding gene,
2. making extracts of the host cell (and optionally purify the CDC27A protein) and than,
3. use it in biological assays in comparison with a wild-type CDC27A cell extract (or purified protein).

Such biological assay may involve a test in response to hormones and sugar and a comparison of the RT-PCR profile of the investigated protein with the profiles of CDC27A.

Another test to investigate the functionality of a CDC27A protein (or a fragment, a homologue or derivative thereof) is a yeast complementation assay, wherein the gene/protein under investigation is introduced in a yeast cell missing its natural cdc27 gene and/or protein. Subsequently it is checked if these yeast cell are able to form colonies normally and if they are capable of normal DNA synthesis. Such a yeast complementation assay has been described by Blilou et al. (Genes Dev. 2002 16(19): 2566-75). In brief, to investigate whether the CDC27A protein can act as a component of the APC, the full-size cDNA can be cloned in a yeast vector with a thiamine-repressible promoter and transformed into an *S. pombe* nuc2$^{ts}$ strain. The cdc27A expression should at least partially rescue the nuc2 phenotype at the restrictive temperature, and reproducibly restore growth to higher density compared with the empty vector control.

Another assay to test the functionality of a cdc27 protein is a "pull down" experiment. CDC27 is part of a multiprotein APC complex, by binding to specific proteins within this complex. To confirm that this protein is indeed implicated in this structure, the tandem affinity purification (TAP) method can be used. The TAP is a tool that allows rapid purification under native conditions of complexes, even when expressed at their natural level. The TAP method requires fusion of the TAP tag, either N- or C-terminally, to the target protein of interest, for example CDC27. By successive elution from affinity columns for the tags, high specific purification of the complex can be obtained. After final elution step of the purified complex, the identification of proteins interacting with the given target protein is done via mass spectrometry. (Puig et al, (2001) The tandem affinity purification (TAP) method: a general procedure of protein complex purification. Methods 24(3):218-29; Rigaut et al. (1999), A generic protein purification method for protein complex characterization and proteome exploration. Nat Biotechnol. 17(10):1030-2).

An example of a further variant cdc27a nucleic acid is a sequence that is capable of hybridising to a cdc27a. Advantageously, the methods according to the present invention may also be practised using sequences capable of hybridising to a cdc27a, particularly a cdc27a as represented by any one of SEQ ID NO: 1 or SEQ ID NO: 3, which hybridising sequences are preferably those falling within the definition of a "cdc27a", meaning that upon construction of a phylogenetic tree, such as the one depicted in FIG. 7, the hybridising sequence would be one that tends to cluster around the cdc27a's. Hybridising sequences suitable for use in the methods according to the invention may readily be determined using routine techniques, such as by assaying for CDC27A activity and/or by following the methods described in the Examples section by simply substituting the sequence used in the actual Example with the hybridising sequence.

The term "hybridisation" as defined herein is a process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and Na$_3$-citrate) and/or the inclusion of formamide in the hybridisation buffer and/or lowering the concentration of compounds such as SDS (detergent) in the hybridisation buffer and/or exclusion of compounds such as dextran sulphate or polyethylene glycol (promoting molecular crowding) from the hybridisation buffer. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. Sufficiently low stringency hybridisation conditions are particularly preferred (at least in the first instance) to isolate nucleic acids heterologous to the DNA sequences of the invention defined supra. An example of low stringency conditions is 4-6×SSC/0.1-0.5% w/v SDS at 37-45° C. for 2-3 hours. Depending on the source and concentration of the nucleic acid involved in the hybridisation, alternative conditions of stringency may be employed, such as medium stringency conditions. Examples of medium stringency conditions include 1-4×SSC/0.25% w/v SDS at $\geq$45° C. for 2-3 hours. An example of high stringency conditions includes 0.1-1×SSC/0.1% w/v SDS at 60° C. for 1-3 hours. The skilled man will be aware of various parameters which may be altered during hybridisation and washing and which will either maintain or change the stringency conditions. The stringency conditions may start low and be progressively increased until there is provided a hybridising cdc27a nucleic acid, as defined hereinabove. Elements contributing to heterology include allelism, degeneration of the genetic code and differences in preferred codon usage.

Another example of a variant cdc27a is an alternative splice variant of a cdc27a. The methods according to the present invention may also be practised using an alternative splice variant of a cdc27a nucleic acid/gene. The term "alternative splice variant" as used herein encompasses variants of a nucleic acid in which selected introns and/or exons have been excised, replaced or added. Such splice variants may be found in nature or can be manmade using techniques well known in the art. A splice variant useful in the methods according to the invention is preferably a "cdc27a", meaning that upon construction of a phylogenetic tree, such as the one depicted in FIG. 7, the splice variant of interest would be one tending to cluster around the cdc27a's rather than around any of the other CDK groups. Preferably, the splice variant is a splice variant of the sequence represented by any of SEQ ID NO: 1 or SEQ ID NO: 3. Splice variants suitable for use in the methods according to the invention may readily be determined using routine techniques, such as by assaying for CDC27A activity and/or by following the methods described in the Examples section by simply substituting the sequence used in the actual Example with the splice variant.

Another example of a variant cdc27a is an allelic variant. Advantageously, the methods according to the present invention may also be practised using allelic variants of a cdc27a nucleic acid, preferably an allelic variant of a sequence represented by any of SEQ ID NO: 1 or SEQ ID NO: 3. Allelic variants exist in nature and encompassed within the methods of the present invention is the use of these isolated natural alleles in the methods according to the invention. Allelic variants encompass Single Nucleotide Polymorphisms (SNPs), as well as Small Insertion/Deletion Polymorphisms (INDELs). The size of INDELs is usually less than 100 bp). SNPs and INDELs form the largest set of sequence variants in naturally occurring polymorphic strains of most organisms. The allelic variants useful in the methods according to the invention are preferably "cdc27a", meaning that upon construction of a phylogenetic tree, such as the one depicted in FIG. 7, the allelic variant of interest would tend to cluster around the cdc27a's. Allelic variants suitable for use in the methods according to the invention may readily be determined using routine techniques, such as by assaying for CDC27A activity and/or by following the methods described in the Examples section by simply substituting the sequence used in the actual Example with the allelic variant.

Accordingly, the present invention provides a method for changing plant development, wherein the cdc27a nucleic acid sequence is a splice variant of a cdc27a nucleic acid sequence or wherein said CDC27A protein is encoded by a splice variant or wherein the cdc27a nucleic acid sequence is an allelic variant of a cdc27a nucleic acid sequence or wherein said CDC27A protein is encoded by an allelic variant.

Examples of variant CDC27A amino acids include homologues, derivatives and active fragments of a CDC27A protein. Advantageously, the methods according to the present invention may also be practised using homologues, derivatives or active fragments of a CDC27A, preferably using homologues, derivatives or active fragments of a CDC27A's as represented by any one of SEQ ID NO: 2 or SEQ ID NO: 4.

"Homologues" of a CDC27A protein encompass peptides, oligopeptides, polypeptides, proteins and enzymes having amino acid substitutions, deletions and/or insertions relative to the unchanged protein in question and having similar biological and functional activity as the unchanged protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

The homologues useful in the methods according to the invention have a percentage identity to SEQ ID NO 2 or 4 equal to value lying between 47% and 99.99%.

The homologues useful in the method according to the invention have at least 47%, 48%, 49% or 50% sequence identity or similarity (functional identity) to the unchanged protein, alternatively at least 60% sequence identity or similarity to an unchanged protein, alternatively at least 70% sequence identity or similarity to an unchanged protein. Typically, the homologues have at least 80% sequence identity or similarity to an unchanged protein, preferably at least 85%, 86%, 87%, 88%, 98% sequence identity or similarity, further preferably at least 90%, 91%, 92%, 93%, 94% sequence identity or similarity to an unchanged protein, most preferably at least 95%, 96%, 97%, 98% or 99% sequence identity or similarity to an unchanged protein.

The percentage of identity can be calculated by using an alignment program well known in the art. For example, the percentage of identity can be calculated using the program GAP, or needle (EMBOSS package) or stretcher (EMBOSS package) or the program align X, as a module of the vector NTI suite 5.5 software package, using the standard parameters (for example GAP penalty 5, GAP opening penalty 15, GAP extension penalty 6.6).

The homologues useful in the methods according to the invention are preferably "cdc27a", meaning that upon construction of a phylogenetic tree, such as the one depicted in FIG. 7, the homologue of interest would tend to cluster around the CDC27A. A preferred CDC27A homologue has more sequence identity with the Arabidosis thaliana cdc27A protein (SEQ ID NO 1) than to another Arabidopsis thaliana protein (for example the Arabidopsis thaliana CDC27B protein, genbank accession number CAD31951). The sequence identity between AtCDC27A and AtCDC27B is 46.8% when calculated with the alignX program as mentioned above. Therefore, preferred homologues useful in the methods of the present invention are homologues having more than 47% sequence identity with AtCDC27A. Homologues suitable for use in the methods according to the invention may readily be determined using routine techniques, such as by assaying for CDC27A activity and/or by following the methods described in the Examples section by simply substituting the sequence used in the actual Example with the homologous sequence.

Methods for the search and identification of CDC27A homologues or DNA sequences encoding a CDC27A homologue, would be well within the realm of persons skilled in the art. Such methods, involve screening sequence databases with the sequences as provided by the present invention in SEQ ID NO 1 and 2, preferably a computer readable format of the nucleic acids of the present invention. This sequence information is available for example in public databases, that include but are not limited to Genbank (http://www.ncbi.nlm.nih.gov/web/Genbank), the European Molecular Biology Laboratory Nucleic Acid Sequence Database (EMBL) (http:/w.ebi.ac.uk/ebi-docs/embl-db.html) or versions thereof or the MIPS database (http://mips.gsf.de/). Different search algorithms and software for the alignment and comparison of sequences are well known in the art. Such software includes software include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percentage sequence identity and performs a statistical analysis of the similarity between the two sequences. The suite of programs referred to as BLAST programs has 5 different implementations: three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., Genome Analysis, 1: 543, 1997). The software for performing BLAST analysis is publicly available through the National Centre for Biotechnology Information.

Homologues of SEQ ID NO 2 can be found in many prokaryotic and eukaryotic organisms. The closest homologues are found in the plant kingdom. For example, partial cdc27a nucleic acids were isolate from rice (SEQ ID NO 5) encoding a rice cdc27 homologue (SEQ ID NO 6), from sugar cane (SEQ ID NO 7 and 8), from maize (SEQ ID NO 9 and 10), from sorghum (SEQ ID NO 11 and 12) and from wheat (SEQ ID NO 13 and 14).

As more genomes are being sequenced, it is expected that many more CDC27A homologues shall be identifiable.

These above-mentioned analysis for comparing sequences, is preferentially done on a full-length sequence or alternatively can be based on a comparison of certain regions such as conserved domains.

The identification of such domains, would also be well within the realm of a person skilled in the art and involves for example, a computer readable format of the nucleic acids of the present invention, the use of alignment software programs and the use of publicly available information on protein domains, conserved motifs and boxes. This protein domain information is available in the PRODOM (http://www.biochem.ucl.ac.uk/bsm/dbbrowser/jj/prodomsrchjj.html), PIR (http://pir.georgetown.edu/) or pFAM (http://pfam.wustl.edu/) database. Sequence analysis programs designed for motif searching can be used for identification of fragments, regions and conserved domains as mentioned above. Preferred computer programs would include but are not limited to MEME, SIGNALSCAN, and GENESCAN. A MEME algorithm (Version 2.2) can be found in version 10.0 of the GCG package; or on the Internet site http://www.sdsc.edu/MEME/meme. SIGNALSCAN version 4.0 information is available on the Internet site http://biosci.cbs.umn.edu/software/sigscan.html. GENESCAN can be found on the Internet site http://gnomic.stanford.edu/GENESCANW.html.

More particularly preferred cdc27A homologues have the conserved domains as described in WO0102430, which text on domains is incorporated herein by reference. More particularly they comprise TRP domain repeats (Interpro database accession number IPR001440 repeat domain) and/or the so-called cdc27/NUC-like domain (prodom database accession number PD555428) or a domain which aligns with these domains when scanned with the above mentioned software for domain identification.

Two special forms of homology, orthologous and paralogous, are evolutionary concepts used to describe ancestral relationships of genes. The term "paralogous" relates to gene-duplications within the genome of a species. The term "orthologous" relates to homologous genes in different organisms due to ancestral relationship. The term "homologues" as used herein also encompasses paralogues and orthologues and are useful proteins in the methods according to the invention.

Another variant of CDC27A useful in the methods of the present invention is a derivative of CDC27A. The term "derivatives" refers to peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" of a CDC27A protein encompass peptides, oligopeptides, polypeptides, proteins and enzymes which may comprise naturally occurring changed, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence such as, for example, a reporter molecule which is bound to facilitate its detection, and non-naturally occurring amino acid residues relative to the amino acid sequence of a naturally-occurring protein.

"Substitutional variants" of a protein are those in which at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues, and deletions will range from about 1 to 20 residues. Preferably, amino acid substitutions comprise conservative amino acid substitutions.

"Insertional variants" of a protein are those in which one or more amino acid residues are introduced into a predetermined site in a protein. Insertions can comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase-tag, protein A, maltose-binding protein, dihydrofolate reductase, Tag-100 epitope, c-myc epitope, FLAG®-epitope, lacZ, CMP (calmodulin-binding peptide), HA epitope, protein C epitope and VSV epitope.

"Deletion variants" of a protein are characterised by the removal of one or more amino acids from the protein. Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Another variant of CDC27A useful in the methods of the present invention is an active fragment of CDC27A. "Active fragments" of a CDC27A protein encompasses contiguous amino acid residues of a CDC27A protein, which residues retain similar biological and/or functional activity to the naturally occurring protein. For example, useful fragments comprise at least 10 contiguous amino acid residues of a CDC27A protein. Other preferred fragments are fragments of the CDC27A protein starting at the second or third or further internal methionin residues. These fragments originate from protein translation, starting at internal ATG codons.

According to a preferred aspect of the present invention, enhanced or increased expression of a cdc27a nucleic acid in a plant or plant part is envisaged. Methods for obtaining increased expression of genes or gene products are well documented in the art and include, for example, overexpression driven by a (strong) promoter, the use of transcription enhancers or translation enhancers. The term overexpression as used herein means any form of expression that is additional to the original wild-type expression level. Preferably the nucleic acid to be introduced into the plant and/or the nucleic acid that is to be overexpressed in the plants is in the sense direction with respect to the promoter to which it is operably linked.

Accordingly, a preferred embodiment of the present invention provides a method to change development in a plant, comprising introducing, into a plant, a nucleic acid sequence capable of increasing or decreasing expression of a cdc27a gene and/or capable of increasing or decreasing activity and/or level of a CDC27A protein in the sense orientation relative to control element to which it is operably linked.

Alternatively and/or additionally, increased expression of a CDC27A encoding gene or increased activities and/or levels of a CDC27A protein in a plant cell, is achieved by mutagenesis. For example these mutations can be responsible for the changed control of the cdc27a gene, resulting in more expression of the gene, relative to the wild-type gene. Mutations can also cause conformational changes in a protein, resulting in more activity and/or levels of the CDC27A protein.

Since accelerated rate of development has been demonstrated via plants overexpressing the cdc27a gene, there is envisaged by the present invention a method for delaying development comprising downregulation of expression of a cdc27a gene or downregulation of levels and/or activity of a CDC27A protein. Also methods encompassing downregulation of CDC27A can be used to decrease the number or the size of organs or to delay flowering. Therefore, according to a further aspect of the invention, decreased expression of a cdc27a nucleic acid or decreased activity and/or level of a CDC27A is envisaged.

Examples of decreasing or downregulation of expression are well documented in the art and include, for example, downregulation of expression by anti-sense techniques, RNAi techniques, small interference RNAs (siRNAs), microRNA (mRNA), etc. Therefore according to a particular aspect of the invention, there is provided a method for changing development of plants, including technologies that are based on for example the synthesis of antisense transcripts, complementary to the mRNA of a cdc27a gene.

Another method for downregulation of gene expression or gene silencing comprises use of ribozymes, for example as described in WO9400012 (Atkins et al.), WO9503404 (Lenee et al.), WO0000619 (Nikolau et al.), WO9713865 (Ulvskov et al.) and WO9738116 (Scott et al.).

Gene silencing may also be achieved by insertion mutagenesis (for example, T-DNA insertion or transposon insertion) or by gene silencing strategies as described among others in the documents WO9836083 (Baulcombe and Angell), WO9853083 (Grierson et al.), WO9915682 (Baulcombe et al.) or WO9953050 (Waterhouse et al.).

Expression of an endogenous gene may also be reduced if the endogenous gene contains a mutation. Such a mutant gene may be isolated and introduced into the same or different plant species in order to obtain plants having changed development. Also dominant negative mutants of a cdc27a nucleic acid can be introduced in the cell to decrease the level/and or activity of the endogenous CDC27a protein.

Other methods to decrease the expression of a cdc27a nucleic acid and/or activity and/or level of CDC27A proteins in a cell encompass for example the mechanisms of transcriptional gene silencing, such as the methylation of the cdc27a promoter.

Another mechanism to downregulate levels and/or activity of a CDC27A protein in a plant encompasses the mechanism of co-suppression. Increasing or decreasing gene expression (whether by a direct or indirect approach) encompasses changed transcript levels of that gene. Changed transcript levels can be sufficient to induce certain phenotypic effects, for example via the mechanism of cosuppression. Here the overall effect of expression of a transgene is that there is less activity in the cell of the protein encoded by a native gene having homology to the introduced transgene. Cosuppression is accomplished by the addition of coding sequences or parts thereof in a sense orientation into the cell. Therefore, according to one aspect of the present invention, the development of a plant may be changed by introducing into a plant an additional copy (in full or in part) of a cdc27a gene already present in a host plant. The additional gene may silence the endogenous gene, giving rise to a phenomenon known as co-suppression.

Genetic constructs aimed at silencing gene expression may comprise the cdc27a nucleotide sequence or one at least a portion thereof in a sense and/or antisense orientation relative to the promoter sequence. Preferably the portions comprises at least 21 contiguous nucleic acid of a sequence to be downregulated. Also, sense or antisense copies of at least part of the endogenous gene in the form of direct or inverted repeats may be utilised in the methods according to the invention. The development of plants may also be changed by introducing into a plant at least part of an antisense version of the nucleotide sequence represented, for example, by SEQ ID NO: 1. It should be clear that part of the nucleic acid (a portion) could also achieve the desired result. Homologous anti-sense genes are preferred, homologous genes being plant genes, preferably plant genes from the same plant species in which the silencing construct is introduced.

The expression of a cdc27a gene can be investigated by northern or Southern blot analysis of cell extracts. The levels of CDC27A protein in the cell can be investigated via Western blot analysis of cell extracts.

The activity of a CDC27A protein can be investigated by making extracts of a cell (and optionally purify the CDC27A protein) and than use it in biological assays in comparison with a wild-type CDC27A cell extract (or purified protein). Such biological assay may involve a test in response to hormones and sugar and a comparison of the RT-PCR profile of the investigated protein with the profiles of CDC27A.

Another test to investigate the functionality of a CDC27A protein (or a fragment, a homologue or derivative thereof) is a yeast complementation assay, wherein the gene/protein under investigation is introduced in a yeast cell missing its natural cdc27 gene and/or protein. Subsequently it is checked if these yeast cell are able to form colonies normally and if they are capable of normal DNA synthesis. Such a yeast complementation assay has been described by Blilou et al. (Genes Dev. 2002 16(19): 2566-75). In brief, to investigate whether the CDC27A protein can act as a component of the APC, the full-size cDNA can be cloned in a yeast vector with a thiamine-repressible promoter and transformed into an *S. pombe* nuc2$^{ts}$ strain. The cdc27A expression should at least partially rescue the nuc2 phenotype at the restrictive temperature, and reproducibly restore growth to higher density compared with the empty vector control.

Another assay to test the functionality of a cdc27 protein is a "pull down" experiment. CDC27 is part of a multiprotein APC complex, by binding to specific proteins within this complex. To confirm that this protein is indeed implicated in this structure, the tandem affinity purification (TAP) method can be used. The TAP is a tool that allows rapid purification under native conditions of complexes, even when expressed at their natural level. The TAP method requires fusion of the TAP tag, either N- or C-terminally, to the target protein of interest, for example CDC27. By successive elution from affinity columns for the tags, high specific purification of the complex can be obtained. After final elution step of the purified complex, the identification of proteins interacting with the given target protein is done via mass spectrometry. (Puig et al, (2001) The tandem affinity purification (TAP) method: a general procedure of protein complex purification. Methods 24(3):218-29; Rigaut et al. (1999), A generic protein purification method for protein complex characterization and proteome exploration. Nat Biotechnol. 17(10):1030-2).

According to second embodiment of the present invention, genetic constructs and vectors to facilitate introduction and/or expression of the nucleotide sequences useful in the methods according to the invention are provided. Therefore, according to the second embodiment, the present invention provides a genetic construct comprising:

(i) a nucleic acid sequence capable of increasing or decreasing expression of a cdc27a nucleic acid and/or capable of increasing or decreasing the activity and/or level of a CDC27A protein;

(ii) one or more control sequences capable of regulating expression of the nucleic acid sequence of (i); and optionally (iii) a transcription termination sequence.

According to the methods of the present invention, such a vector is introduced into a plant or plant part.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

The genetic construct can be an expression vector wherein said nucleic acid sequence is operably linked to one or more control sequences allowing expression in prokaryotic and/or eukaryotic host cells.

The nucleic acid according to (i) is advantageously any of the aforementioned nucleic acids, preferably a cdc27a nucleic acid, most preferably a cdc27a nucleic acid according to SEQ ID NO 1 or 3. The construct sequence of (ii) is preferably a constitutive promoter, for example a CaMV35S or GOS2 promoter The methods according to the present invention may also be practised by introducing into a plant at least a part of a (natural or artificial) chromosome (such as a Bacterial Artificial Chromosome (BAC)), which chromosome contains at least a cdc27a gene/nucleic acid, optionally together with one or more related gene family members. Therefore, according to a further aspect of the present invention, there is provided a method for changing plant development by introducing into a plant at least a part of a chromosome comprising at least a cdc27a gene/nucleic, which cdc27a gene/nucleic is preferably one represented by any one of SEQ ID NO: 1 or SEQ ID NO: 3.

According to a preferred embodiment of the invention, the genetic construct is an expression vector designed to overexpress the nucleic acid sequence. The nucleic acid sequence capable of increasing or decreasing expression of a cdc27a nucleic acid and/or activity and/or level of a CDC27A protein itself may be a cdc27a nucleic acid or a homologue, derivative or active fragment thereof, such as any of the nucleic acid sequences described hereinbefore. A preferred nucleic acid sequence is the sequence represented by SEQ ID NO: 1 or 3 or a portion thereof or sequences capable of hybridising therewith or a nucleic acid sequence encoding a sequence represented by SEQ ID NO: 2 or 4 or a homologue, derivative or active fragment thereof. Preferably, this nucleic acid is cloned in the sense orientation relative to the control sequence.

Plants are transformed with a vector comprising the sequence of interest (i.e., the nucleic acid sequence capable of increasing or decreasing expression of cdc27a nucleic acid), which sequence is operably linked to one or more control sequences (at least a promoter). The terms "regulatory element", "control sequence" and "promoter" are all used herein interchangeably and are to be taken in a broad context to refer to regulatory nucleic acid sequences capable of effecting expression of the sequences to which they are ligated (i.e. operably linked). Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence depending on the desired outcome. For example, a meristem-specific promoter, such as the rnr (ribonucleotide reductase), cdc2a promoter and the cyc07 promoter. Also seed-specific promoter, such as p2S2, pPROLAMIN, pOLEOSIN could be selected. An aleurone-specific promoter may be selected. An inflorescence-specific promoter, such as pLEAFY, may also be utilised. To produce male-sterile plants one would need an anther specific promoter. One could also choose a petal-specific promoter. If the desired outcome would be to change development in particular organs, then the choice of the promoter would depend on the organ to be changed. For example, use of a root-specific promoter would lead to phenotypic alteration of the root. This would be particularly important where it is the root itself that is the desired end product; such crops include sugar beet, turnip, carrot, and potato. A fruit-specific promoter may be used to modify, for example, the strength of the outer skin of the fruit or to increase the size of the fruit. A green tissue-specific promoter may be used to influence the phenotype of the leaf. A cell wall-specific promoter may be used to increase the rigidity of the cell wall, thereby increasing pathogen resistance. An anther-specific promoter may be used to produce male-sterile plants. A vascular-specific promoter may be used to increase transport from leaves to seeds. A nodule-specific promoter may be used to increase the nitrogen fixing capabilities of a plant, thereby increasing the nutrient levels in a plant. A stress-inducible promoter may also be used to drive expression of a nucleic acid during conditions of stress. A stress inducible promoter such as the water stress induced promoter WSI18, the drought stress induced Trg-31 promoter, the ABA related promoter rab21 or any other promoter which is induced under a particular stress condition such as temperature stress (cold, freezing, heat) or osmotic stress, or drought stress or oxidative stress or biotic stress can be used to drive expression of a cdc27a gene.

Preferably, the nucleic acid sequence capable of increasing or decreasing expression of a cdc27a gene is operably linked to a constitutive promoter. The term "constitutive" as defined herein refers to a promoter that is expressed predominantly in at least one tissue or organ, and predominantly at any life stage of the plant. Preferably the promoter is expressed predominantly in most tissues or organs of the plant, most preferably throughout the whole plant. Preferably, the constitutive promoter is a CaMV35s promoter or GOS2 promoter, or a promoter of similar strength and/or a promoter with a similar expression pattern. Similar strength and/or similar expression pattern can be analysed for example by coupling the promoters to a reporter gene and check the function of the reporter gene in tissues of the plant. One suitable reporter gene is beta-glucuronidase and the colorimetric GUS staining to visualize the reporter gene activity in a plant tissue is well known to a person skilled in the art. Examples of other constitutive promoters are presented in Table 1, which promoters or derivatives thereof are useful in performing the methods of the present invention.

TABLE 1

EXEMPLARY CONSTITUTIVE PROMOTERS FOR USE IN THE PERFORMANCE OF THE PRESENT INVENTION

| GENE SOURCE | EXPRESSION PATTERN | REFERENCE |
|---|---|---|
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant. 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| rice cyclophilin | constitutive | Buchholz et al, Plant Mol Biol. 25(5): 837-43, 1994 |
| maize H3 histone | constitutive | Lepetit et al, Mol. Gen. Genet. 231: 276-285, 1992 |
| actin 2 | constitutive | An et al, Plant J. 10(1); 107-121, 1996 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences, which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene, which confers a phenotype on a cell in which it is expressed to facilitate the identification and/or selection of cells which are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII encoding neomycin phosphotransferase capable of phosphorylating neomycin and kanamycin, or hpt encoding hygromycin phosphotransferase capable of phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example beta-glucuronidase, GUS), luminescence (such as luciferase) or fluorescence (Green Fluorescent Protein, GFP, and derivatives thereof. Further examples of suitable selectable marker genes include the ampicillin resistance (Ampr), tetracycline resistance gene (Tcr), bacterial kanamycin resistance gene (Kanr), phosphinothricin resistance gene, and the chloramphenicol acetyltransferase (CAT) gene, amongst others In a preferred embodiment, the genetic construct as mentioned above, comprises a cdc27a nucleic acid in the sense orientation coupled to a promoter that is preferably a constitutive promoter, such as for example the GOS2 promoter. Therefore according to another aspect of the invention, there is provided an isolated nucleic acid, comprising an expression cassette, comprising at least a part of a nucleic acid sequence depicted in SEQ ID NO 1 or 3, or the complementary strand thereof; operably linked to at least a part of a constitutive promoter.

According to a third embodiment of the present invention, there is provided a method for the production of a plant having changed development, comprising increasing or decreasing expression and or activity and/or levels in a plant of a cdc27a nucleic acid or CDC27A protein. According to a particular embodiment, the present invention provides a method for the production of transgenic plants having changed growth characteristics, which method comprises:

(i) introducing into a plant or plant part a nucleic acid or a portion thereof or sequences capable of hybridising therewith, which nucleic acid is capable of increasing or decreasing expression of a cdc27a gene and/or capable of increasing or decreasing the activity and/or levels of a CDC27A, preferably wherein said nucleic acid encodes a CDC27A protein or a homologue, derivative or active fragment thereof;

(ii) cultivating the plant cell under conditions promoting regeneration and mature plant growth.

The nucleic acid of (i) may advantageously be any of the aforementioned nucleic acids, preferably a cdc27a nucleic acid, most preferably a cdc27a nucleic acid according to SEQ ID NO 1 or 3. The nucleic acid is preferably operably linked to a constitutive promoter such as a CaMV35S or GOS2 promoter.

The protein itself and/or the nucleic acid itself may be introduced directly into a plant cell or into the plant itself (including introduction into a tissue, organ or any other part of the plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g. cotyledon meristem and hypocotyl meristem). The polynucleotide may be transiently or stably introduced into a host cell and may be maintained non-integrated, for example, as a plasmid. Alternatively and preferably, the transgene may be stably integrated into the host genome. The resulting transformed plant cell can then be used to regenerate a transformed plant in a manner known to persons skilled in the art.

Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like.

Transgenic rice plants expressing a cdc27a gene are preferably produced via *Agrobacterium*-mediated transformation using any of the well known methods for rice transformation, such as described in any of the following: published European patent application EP 1198985 A1, Aldemita and Hodges (Planta, 199, 612-617, 1996); Chan et al. (Plant Mol. Biol. 22 (3) 491-506, 1993), Hiei et al. (Plant J. 6 (2) 271-282, 1994), which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention also encompasses plants obtainable by the methods according to the present invention. The present invention therefore provides plants obtainable by the method according to the present invention, which plants have changed development, when compared to the wild-type plants and which plants have increased or decreased CDC27A protein activity and/or levels and/or increased or decreased expression of a cdc27a nucleic acid.

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention accordingly also includes host cells containing an isolated nucleic acid molecule encoding a CDC27A protein. Preferred host cells according to the invention are plant cells. The invention also extends to harvestable parts of a plant such as but not limited to seeds, leaves, fruits, flowers, stem cultures, stem, rhizomes, roots, tubers and bulbs.

Preferably said plants are transformed with a CDC27A encoding gene under the control of a constitutive promoter and more preferably the plants of the present invention carry an expression cassette comprising at least a part of cdc27A and at least a part of a constitutive promoter as mentioned hereinabove. The host cells, plants or the plant parts of the present invention can be identified by the presence of higher expression of a cdc27a gene and/or or a higher level and/or activity of a cdc27A protein. Further, particular plants of the present invention are recognizable by the presence of a cdc27a transgene or part thereof genetically coupled to a constitutive promoter, preferably to a CaMV35S promoter or to a GOS2 promoter or any promoter as described hereinabove, or at least a part thereof.

The term "plant" as used herein encompasses whole plants, ancestors and progeny of the plants and plant parts, including seeds, shoots, stems, roots (including tubers), and plant cells, tissues and organs. The term "plant" also therefore encompasses suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divancata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feioa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus*

*communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbiratus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of the present invention. Preferably the plant according to the present invention is a crop plant selected from rice, maize, wheat, barley, soybean, sunflower, canola, sugarcane, alfalfa, millet, leguminosae (bean, pea), flax, lupinus, rapeseed, tobacco, popular and cotton. Further preferably, the plant according to the present invention is a monocotyledonous plant, most preferably a cereal.

The term development as used herein means the process to reach maturity and reproductive stage, involving differentiation of the cells and organ formation.

A change in development means a change in time to reach maturity as well as a change in developmental characteristics which are manifestations of development such as differentiation and/or organ formation.

Advantageously, the present invention provides a method to change plant development, wherein the changed development is preferably selected from changed differentiation, changed rate of development, changed organ formation, changed organ size and/or number, and changed reproductive characteristics, relative to the wild-type plants.

Further preferably, the changed differentiation is accelerated differentiation and/or the changed rate of development is accelerated rate of development and/or the changed organ formation is accelerated organ formation and/or the changed organ size and/or number is increased organs size and/or number and/or the changed reproductive characteristic is early flowering and increased number of flowers and/or seeds.

The plants according to the present invention show accelerated differentiation. This feature is particularly advantageous for accelerating crop production.

The plants according to the present invention show accelerated rate of development. Therefore, in addition to the accelerated rate of differentiation (which is typically a phenomenon for cells leaving the meristem), the faster rate of development is manifested in more than one part of a plant and throughout the life of the plant. The effects of a cdc27A may also be more pronounced in more mature stages of the plant.

The plants according to the present invention, show accelerated organ formation. More particularly, the formation of leaves, flowers and seeds is accelerated. These features are particularly interesting for horticultural applications as well as agriculture, in particular for crop plants harvested for their green biomass (grasses), flowers (cotton) or their seeds (cereals).

The plants according to the present invention have increased size and number, more particularly bigger leaves, longer leaves, wider leaves, more leaves, longer stem, more flowers, more seed pods, more seeds.

The methods of the present invention clearly change the appearance or morphology of a plant, including any one or more structural features or combination of structural features thereof. Therefore the plants according to the present invention have changed architecture when compared to the wild-type plants. Other structural features, which may be altered by the methods of the present invention include shape, size, number, position, texture, arrangement, and pattern of any cell, tissue or organ or groups of cells, tissues or organs of a plant, including the root, leaf, shoot, stem or tiller, petiole, trichome, flower, inflorescence (for monocotyledonous and dicotyledonous plants), panicles, petal, stigma, style, stamen, pollen, ovule, seed, embryo, endosperm, seed coat, aleurone, fibre, cambium, wood, heartwood, parenchyma, aerenchyma, sieve elements, phloem or vascular tissue, amongst others.

The plants according to the present invention have changed reproductive characteristics. The term "reproductive characteristic" as used herein encompasses the characteristics, which are involved in flowering time, time to reach the flowering stage and the reproductive organs (such as for example flowers and flowers parts and the seeds). More particularly, the plants of the present invention show early flowering, relative to corresponding wild-type plants. The characteristic of early flowering is particularly favourable for any crop plant, since the life cycle (i.e. cycling time) of the plants is reduced and harvesting can take place sooner. Consequently the agricultural land is available sooner for further crops. Also land, which is normally not available for agriculture because of the too short growing season, may now become accessible for the plants of the present invention.

The plans according to the present invention have more flowers and seeds and therefore have increased yield.

The term "increased yield" encompasses an increase in biomass in one or more parts of a plant relative to the biomass of corresponding wild-type plants. The term also encompasses an increase in seed yield, which includes an increase in the biomass of the seed (seed weight) and/or an increase in the number of (filled) seeds and/or in the size of the seeds and/or an increase in seed volume, each relative to corresponding wild-type plants. An increase in seed size and/or volume may also influence the composition of seeds. An increase in seed yield could be due to an increase in the number and/or size of flowers. An increase in yield might also increase the harvest index, which is expressed as a ratio of the total biomass over the yield of harvestable parts, such as seeds.

Accordingly, a particular embodiment of the present invention relates to a method to increase seed yield and/or to increase harvest index of a cereal. The methods of the present invention are therefore particularly favourable to be applied to crop plants, preferably seed crops and cereals, because the methods of the present invention are used to increase the seed yield and harvest index of the plant. Therefore, the methods of the present invention are particularly useful for plants grown for harvest of seeds, such as cereals, rapeseed, sunflower, leguminosae (e.g. soybean, pea, bean) flax, lupinus, canola etc. . . .

Additionally or alternatively, the plants according to the invention have more leaves and bigger stems. Therefore, the methods of the present invention are additionally and/or alternatively particularly favourable to crops grown for the green tissue and/or grown for the above ground biomass. The methods of the present invention are particularly useful for increasing leaf size and number of grasses and forage crops (such as forage maize, clover, *medicago* alfalfa etc.). The methods of the present invention are also particularly useful for increasing the stem size of trees (for paper and pulp industry) and sugar cane.

The present invention also relates to use of a cdc27a nucleic acid and to the use of portions thereof or nucleic acids hybridising therewith in changing development, differentiation and organ formation of plants. The present invention also relates to use of a CDC27A protein and to the use of homologues, derivatives and active fragments thereof in changing development, differentiation and organ formation of plants. The nucleic acid sequence is preferably as represented by SEQ ID NO: 1 or 3 or a portion thereof or sequences capable of hybridising therewith or is an amino acid sequence represented by SEQ ID NO: 2 or 4 or a homologue, derivative or active fragment thereof.

The present invention also relates to the use of a cdc27a nucleic acid and to the use of portions thereof or nucleic acids hybridising therewith and to the use of the CDC27A protein itself and of homologues, derivatives and active fragments thereof as regulators of plant development. The nucleic acid sequences hereinbefore described (and portions of the same and sequences capable of hybridising with the same) and the amino acid sequences hereinbefore described (and homologues, derivatives and active fragments of the same) are useful in changing development of plants, as hereinbefore described. The sequences would therefore find use as regulator of such processes, such as regulators of rate of development, rate of organ formation, regulator of organ number and size, or regulator of reproductive characteristics, such as flowering time, number of flowers and seeds.

The present invention also provides a composition comprising a protein represented by any of the aforementioned amino acid sequences or homologues, derivatives or active fragments thereof for the use as a regulator of developmental processes and characteristics, such as mentioned hereinabove.

Conversely, the sequences according to the present invention may also be interesting targets for agrochemical compounds, such as herbicides or growth stimulators. Accordingly, the present invention encompasses use of the aforementioned nucleic acid sequences (or a portion of the same or sequences capable of hybridising with the same) or an amino acid sequence as hereinbefore described (or homologues, derivatives and active fragments of the same) as targets for an agrochemical compound, such as a herbicide or a growth stimulator.

According to another aspect of the present invention, advantage may be taken of the nucleotide sequence capable of increasing or decreasing expression of a cdc27a nucleic acid in breeding programmes. The nucleic acid sequence may be on a chromosome, or a part thereof, comprising at least the cdc27a nucleic acid sequence and preferably also one or more related family members. In an example of such a breeding programme, a DNA marker is identified which may be genetically linked to a gene capable of increasing or decreasing expression of a cdc27a nucleic acid in a plant, which gene may be a gene encoding the CDC27A protein itself or any other gene which may directly or indirectly influence expression of the cdc27a gene and/or activity of the CDC27A protein itself. This DNA marker may then be used in breeding programs to select plants having changed development.

Further the use of allelic variants as described herein-above are particularly useful for conventional breeding programmes, such as in marker-assisted breeding, which is also encompassed by the present invention. Such breeding programmes sometimes require the introduction of allelic variations in the plants by mutagenic treatment of a plant. One suitable mutagenic method is EMS mutagenesis. Identification of allelic variants then may take place by, for example, PCR. Tilling is preferred for identifying allelic variants. This is followed by a selection step for selection of superior allelic variants of the CDC27A sequence and which give rise to changed development in a plant. Selection, according to the method of the present invention, is typically carried out by monitoring development, differentiation and organ formation of plants containing different allelic variants of the CDC27A sequence, for example, different allelic variants of SEQ ID NO: 1 or of a CDC27A orthologue in that plant. Monitoring growth performance can be done in a greenhouse or in the field. Further optional steps include crossing plants, in which the superior allelic variant was identified, with another plant. This could be used, for example, to make a combination of interesting phenotypic features.

Therefore, mutations in the cdc27a gene may occur naturally, and may form the basis of the selection of plants showing accelerated rate of development, increased organ size and/or number, and/or early flowering.

Accordingly, as another aspect of the invention, there is provided a method for the selection of plants having changed development, which method is based on the selection of better-performing allelic variants of the CDC27A sequence relative to the wild-type allele, and which give rise to changed development in a plant.

According to another aspect of the invention, there is also provided a method for generating plants having changed plant development, when compared to the corresponding wild-type plant, which method comprises the steps of:
a. Growing a plant with increased or decreased expression of a cdc27a nucleic acid sequence and/or having increased or decreased levels and/or activity of a CDC27A protein, when compared to the wild-type plant, and
b. Crossing said plant of (a) with a plant of interest; and
c. Producing progeny of the cross, and optionally,
d. selecting the progeny with said changed development.

Alternatively, the cdc27a gene itself can be used as a (genetic) marker to detect the presence or absence of a desired trait, or Quantitative Trait Locus (QTLs). In this application of the present invention the gene encoding CDC27A is genetically linked to the desired trait, and typically the phenotypes caused by the gene encoding a CDC27A are monitored in order to breed and select plants with the desired trait. This desired trait or QTL, may comprise a single gene or a cluster of linked genes that affect the desired trait.

In molecular biology it is standard practice to select upon transfection or transformation those individuals (or groups of individuals, such as bacterial or yeast colonies or phage plaques or eukaryotic cell clones) that are effectively transfected or transformed with the desired genetic construct. Typically these selection procedures are based on the presence of a selectable or screenable marker in the transfected genetic construct, to distinguish the positive individuals easily from the negative individuals. Therefore, the cdc27a gene can also be used for these purposes, since introduction of this gene into a host cell results in changed development of said host cell.

The methods according to the present invention may also be practised by co-expression of a cdc27a gene in a plant with at least one other gene that cooperates with the cdc27a gene. Co-expression may be effected by cloning the genes under the control of a plant expressible promoter in a plant expressible vector and introducing the expression vector(s) into a plant cell using *Agrobacterium*-mediated plant transformation.

The methods according to the present invention result in plants having changed development, as described hereinbefore. These advantageous developmental characteristics may also be combined with other economically advantageous traits, such as further yield-enhancing traits, tolerance to various stresses, traits increasing or decreasing various architectural features and/or biochemical and/or physiological features. Accordingly, the methods of the present invention can also be used in so-called "gene stacking" procedures.

Also the present invention encompasses a food product derived from any of the plants produced by the methods of the present invention. Further the invention also refers to the use of a product derived from any of the plants according to the present invention in animal feed and in food or in the production procedures thereof.

In a particular embodiment of the invention the plants with improved developmental characteristics are used to produce industrial enzymes and/or pharmaceuticals. The production of such enzymes or pharmaceuticals in plants is aimed at high accumulation of the desired products in a particular and easy to harvest plant tissues, for example accumulation in the leaves and/or in the seeds. The plants of the present invention have bigger stems, bigger leaves, more leaves, more flowers and/or more seeds, and therefore are capable of producing more industrial enzymes and/or pharmaceuticals in these tissues, more particularly in their green biomass and/or in their seeds. Accordingly, the present invention also provides a method for the production of enzymes and/or pharmaceuticals, which method comprises the increasing or decreasing of expression of a cdc27a gene or the increasing or decreasing of activity and/or level of a CDC27A protein. Further the invention relates to the use of plants according to the invention for the production of industrial enzymes and pharmaceuticals and the invention extends to the industrial enzymes and pharmaceuticals produces according to these methods.

DESCRIPTION OF THE FIGURES

The present invention will now be described with reference to the following figures in which:

FIG. 4 is a graphical illustration indicating the length of the leaves 6 (A), and 7 (B) of cdc27a transgenic plants compared to the control line (SR1).

FIG. 6 is the nucleic acid sequence and protein sequence of the *Arabidopsis thaliana* cdc27A proteins (CDC27A1 and CDC27A2) useful for the methods of the present invention. This figure also shows the partial nucleic acid and protein sequences of *Oryza sativa* CDC27 and *Saccharum* sp. CDC27; and *Zea Mays, Sorgum bicolor* and *Triticum aestivum* EST nucleotides and EST protein translations.

EXAMPLES

The present invention will now be described with reference to the following examples, which are by way of illustration alone.

Unless otherwise stated, recombinant DNA techniques are performed according to standard protocols described in Sambrook (2001) Molecular Cloning: a laboratory manual, 3rd Edition Cold Spring Harbor Laboratory Press, CSH, New York; or in Volumes 1 and 2 of Ausubel et al. (1988), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Cloning of the cdc27a Gene

Figure 1:
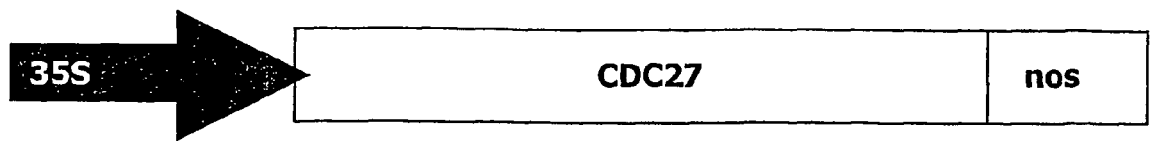
FIG. 1 is a schematic representation of the construct used for transforming the plants of the present invention.

To express constitutively the *Arabidopsis* cdc27a cDNA in transgenic plants, the full-length cdc27a gene was isolated and cloned as follows. To introduce suitable restriction sites in the cdc27a cDNA, a PCR reaction has been carried out using oligonucleotides containing NcoI and BamHI restriction sites. The resulting fragment was restricted with the 2 enzymes (NcoI and BamHI). The cdc27a open reading frame was ligated in the PH35S vector (Hemerly et al. EMBO J. 14, 3925-3936), which was opened with the Nco1 and BamH1 restriction enzymes. The resulting expression cassette contained the CaMV35S promoter, the Atcdc27a gene and the NOS terminator (see FIG. 1). Subsequently, this plasmid was digested with EcoRI, filled in with Klenow enzyme, and then cut with SalI to release the expression cassette containing the 35S promoter, the CDC27 reading frame, and the NOS terminator. This fragment was cloned in the PGSV4 plasmid in the SalI and ScaI sites. The resulting expression plasmid was introduced in *Agrobacterium tumefasciens* C58.

Example 2

Transformation of Tobacco Cells with the 35S::cdc27a Construct

Tobacco plants were transformed with the *Agrobacterium* strain as mentioned in Example 1 comprising the CDC27A expression vector. For introduction of the cdc27a gene into tobacco plants, the leaf disk method was used (Horsch et al., 1985; A simple and general method for transferring genes into plants Science 227 1229-1231). From these transformed leaf disks, T0 plants were regenerated and allowed to sed seeds (T1 seeds). These T1 seeds were germinated in medium containing kanamycin to determine the number of loci of the transgene. Plants with a 3 to 1 relation of kanamycin resistant to susceptible seedlings were chosen to produce seeds in order to obtain homozygous plants.

Example 3 cdc27a Transgenic Tobacco Plants Develop Faster

Wild type tobacco plants and transgenic tobacco plants were simultaneously grown in the same growth conditions.

Figure 2:
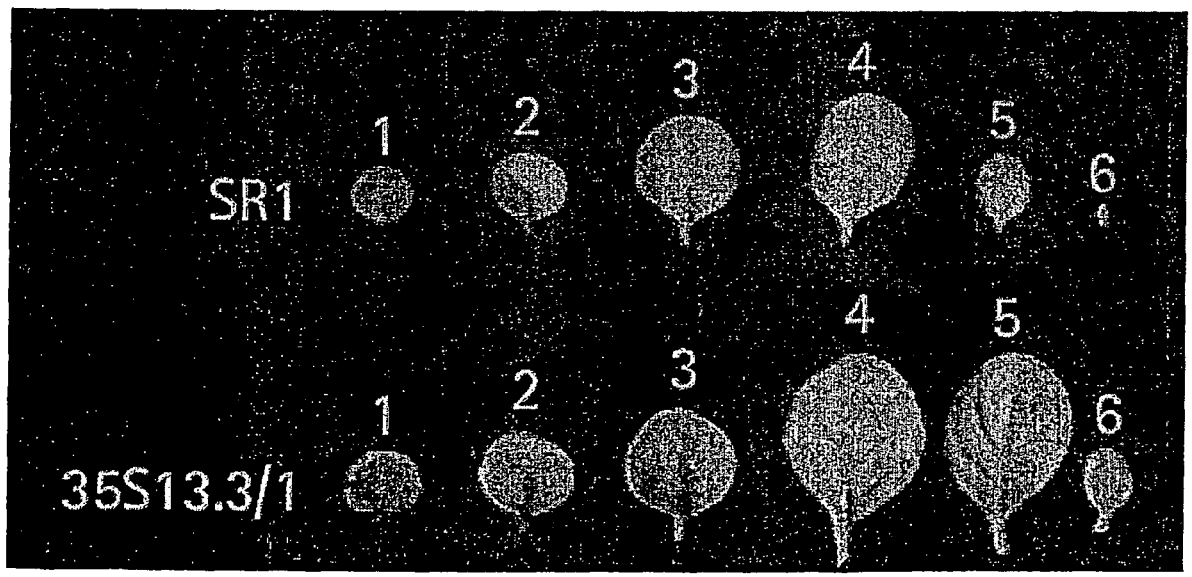
FIG. 2 illustrates that leaves develop faster in cdc27a transgenic plants (35S13.3/1) compared to control plants (SR1). Number 1 to 6 correspond to the leaves as they grow on the stem of the plant, meaning that leaf 1 is the leaf developed in the juvenile plant and leaf 6 being the most recently developed leaf, i.e. a leaf developed when the same plant is in a more mature stage.

The leaves of transgenics and non-transgenic plants were cut off, sorted by age (1 is the oldest leaf and 6 is the newest developed leaf on the stem) and photographed (see FIG. 2).

The upper line designated SR1 shows the leaves of a non-transgenic control plant and the lower line designated 35S13.3/1, shows the leaves of a transgenic plant transformed with the 35S::cdc27a construct. This comparative picture of the leaves at the same age of both plants, illustrates that the transgenic leaves are bigger. Therefore it can be concluded that the transgenic leaves develop faster. It was also observed that the transgenic seedlings produce leaves earlier than the wild-type control plants. Therefore it can be concluded that the developmental program in transgenics progresses faster than that of the wild-type plants. The picture of FIG. 2 further illustrates that the effects of CDC27A on plant development becomes progressively more pronounced as the plant matures. These results illustrate that transgenic plants have an accelerated rate of development.

Further it was demonstrated that the leaves of cdc27a transgenic plants had increased leaf length. Wild type tobacco plants and transgenic tobacco plants were simultaneously grown in the same growth conditions and the leaves 6 and 7 were harvested at several days after sowing (see FIG. 4). This numbering corresponds to the leaf numbering of FIG. 2. It was observed that for the recent leaves 6 and 7, the leaves of the transgenic plants develop quicker (FIGS. 4A and B respectively). This is illustrated by the fact that the transgenic leaves are longer at the same age as the leaves of wild-type. The transgenic leaf 6 is already developed and is 400 mm long on day 45 after sowing, while the leaf 6 of the wild-type plant is just being formed. It is illustrated that the leaves 6 and 7 of the transgenic plant lines (1.1, 1.3, 18.1, 25, 3.2) are longer than that of control line SR1 line. The transgenic leaves were longer than the wild-type leaves at the same age, which age is preferably before the mature stage.

Figure 5:
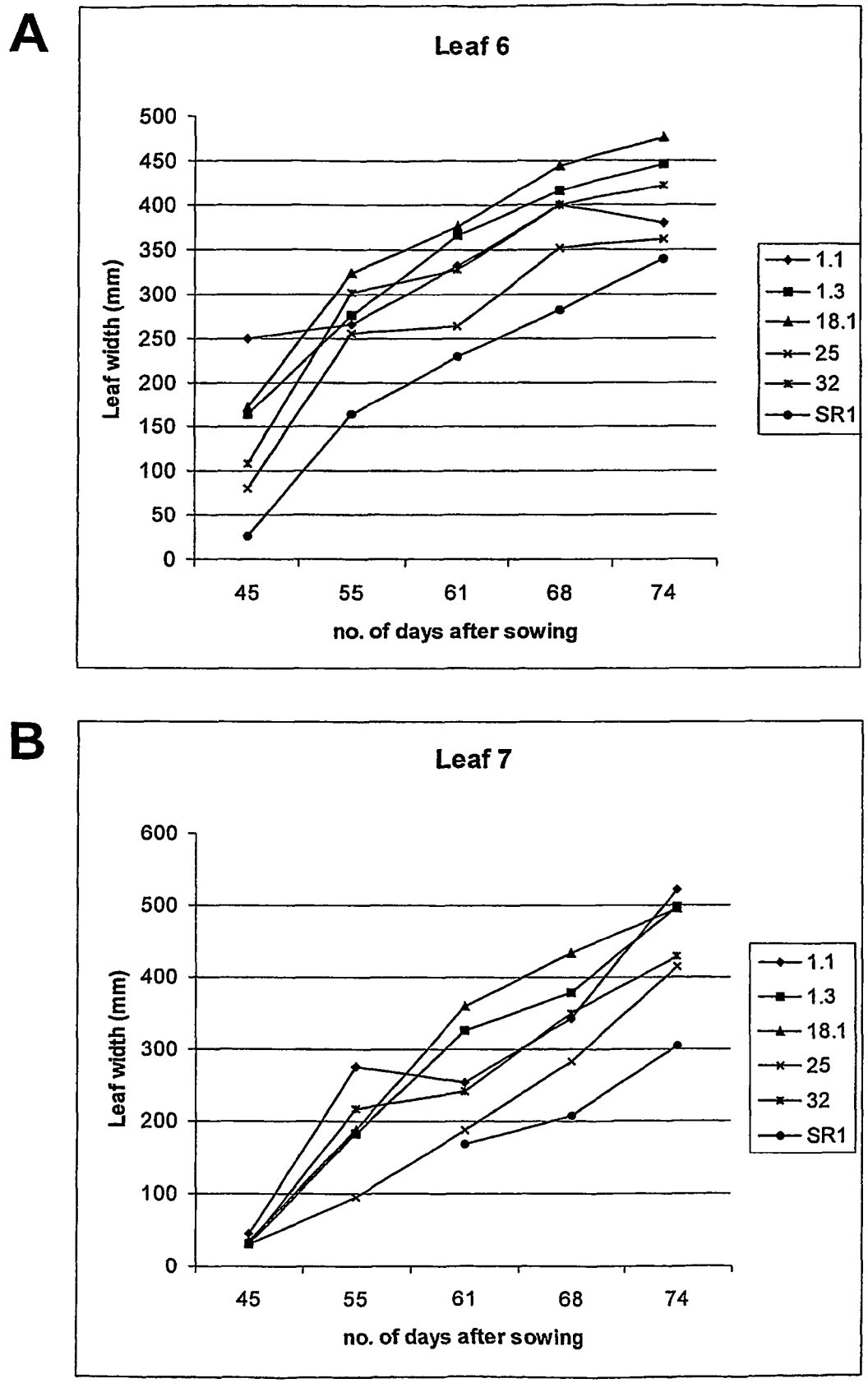
FIG. 5 is a graphical illustration indicating the width of the leaves 6 (A) and 7 (B) of cdc27a transgenic plants compared to the control line (SR1).
Figure 7:
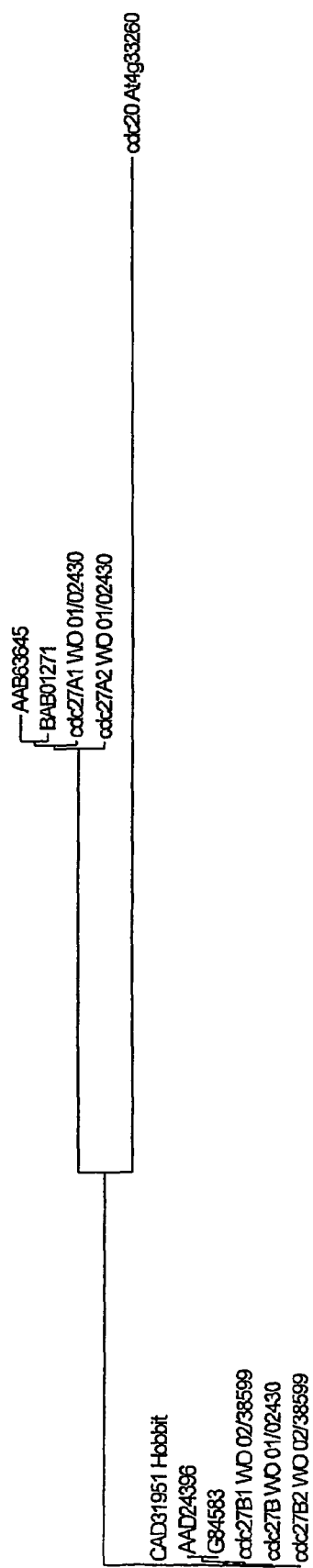
FIG. 7 is a phylogenetic tree showing the structural and evolutionary relationship between A-type cdc27 proteins and B-type cdc27 proteins of *Arabidopsis thaliana*. The tree was construed using the software Align X as part of the VNTi suite 5.5 software package. As an outgroup; the protein sequence of Atcdc20 was used. The sequences are annotated by their Genbank accession number or by the International publication number of the patent application in which they are described.

Further it was demonstrated that the leaves of cdc27a transgenic plants had increased leaf width. Wild type tobacco plants and transgenic tobacco plants were simultaneously grown in the same growth conditions and the leaves 6 and 7 were harvested and measured at several days after sowing (see FIG. 5). This numbering corresponds to the leaf numbering of FIG. 2. It is illustrated that the leaf width of the newly developed leaves 6 and 7 of the transgenic plant lines (1.1, 1.3, 18.1, 25, 3.2) is larger than of the control line SR1.

The transgenic leaves were wider than the wild-type leaves at the same age, which age is preferably before the mature stage.

Example 4 cdc27a Transgenic Plants Show Increased Biomass

Figure 3:
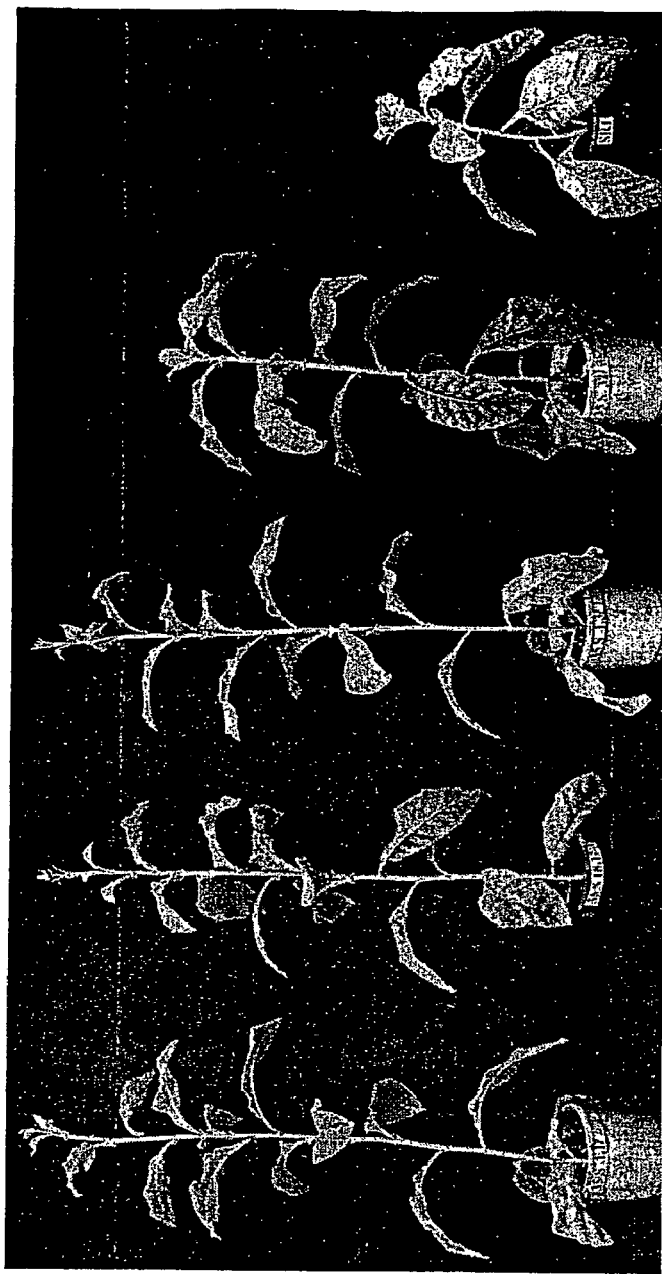
FIG. 3 illustrates transgenic plants transformed with the construct 35S::cdc27a (positions 1 to 4) and a non transgenic control plant (position 5). The plants are photographed at the time when the first plants start to flower. The transgenic plants as can be seen in the illustration are taller.

Wild type tobacco plants and transgenic tobacco plants were simultaneously grown in the same growth conditions and a representative set of plants were photographed when the first plants reached the flowering stage (see FIG. 3).

At this point, the transgenic plants (numbers 1 to 4 in FIG. 3) as can be seen in the illustration are taller and have reached a size, that can be the double or more of the size of non-transgenic plants (number 5 in FIG. 3) grown over the same period of time. Moreover at this time transgenic plants have produced 18 leaves in the mean versus 12 to 13 in the wild-type plants. In conclusion, the increased stem size and leaf number both contribute to the increased total biomass in the cdc27a transgenic plants. The fact that besides leaf size (see example 3) also stem size and also the number of leaves is increased, further supports the finding that CDC27A overexpression accelerates overall vegetative development.

Example 5 cdc27a Transgenic Plants Show Early Flowering

Wild type tobacco plants and transgenic tobacco plants were simultaneously grown in the same growth conditions and the plants were photographed when the transgenic plants started to flower (see FIG. 3). It was observed that the transgenic plants had a reduced period of time to reach flowering. 4 out of 5 transgenics lines flowered within 127 days after sowing while wild-type plants took almost 20 days more (see Table 2).

The transgenic plants formed an inflorescence with perfectly healthy flowers, with no penalty on the vegetative tissues at the time of flowering, no penalty on the number of flowers or number of seeds (see Table 3).

This is noteworthy, since the phenotype of early flowering in many cases is associated with reduction in vegetative biomass, a reduction in number of inflorescence and flowers, and a reduction in seed setting. For example, mutations in the el4 gene result in early flowering and in these plants, the early flowing phenotype is typically associated with reduced total leaf number (Doyle et al. Nature 2002 419: 74-77). Furthermore, in TFL1 mutant plants which flower early, the early flowering phenotype is associated with a penalty on flower structure (Shannon and Meeks-Wagner, 1991 The plant cell 3, 877-892). Also, the early flowering phenotype of ebs mutants is associated with a reduction of seed dormancy, plant size and fertility (Gomez-Mena et al., 2001, The plant cell 13, 1011-1024).

The early flowering phenotype demonstrates that CDC27A overexpression changed plant development.

Example 6 cdc27a Transgenic Plants at the Time of Flowering are Taller than WT Plants at the Time of Flowering Transgenic plants transformed with CDC27A flower earlier than control plants (see column flowering time in Table 2). It was further observed that by the time the transgenic plants have reached the flowering stage, the plants were taller than the non-transgenic control plant at the same stage of flowering (see column plant height at flowering time). From these data it is concluded that the transgenic plants show faster (accelerated rate of development, that they flower early and that they are bigger in size. These data indicate that cdc27a transgenic plants have increased biomass.

Example 7 cdc27a Transgenic Plants have More Flowers than WT Plants

At the time of flowering, the flowers were counted from cdc27a transgenic plants and from wild-type plants grown in the same conditions.

Transgenic plants transformed with 35S::cdc27a have more flowers (see Table 3). Measurements involved five plants of each transgenic line and measurements of the control plants involved two SR1 plants. These data illustrate that the introduction of CDC27A in plant can lead to more than a doubling of the amount of flowers. The number of seed pods is accordingly increases while the size of seed pods was not reduced in the transgenic plants. Therefore, it is envisaged that by using the methods of the present invention also the number of seeds is increased.

TABLE 2

| Line | genotype | flowering time, mean after sowing (in days) * | Plant height mean at flowering time (cm) * | leaf number at flowering time * | Leaf length/width ratio |
|---|---|---|---|---|---|
| 1.1 | homozygous | 126.5 +− 11.13 | 63.8 +− 11.77 | 19.25 +− 1.98 | 1.87 +− 0.327 *** |
| 1.3 | homozygous | 123.3 +− 16.66 | 66.3 +− 24.12 | 17.6 +− 3.75 | 1.76 +− 0.36 *** |
| 18.8 | hemizygous | 124.8 +− 7.17 | 59.9 +− 16.70 | 18.2 +− 1.61 | 1.69 +− 0.28 *** |
| 25 ** | homozygous | 138.5 +− 20.30 | 37.87 +− 19.98 | 17 +− 3.65 | 1.95 +− 0.27 *** |
| 32 | homozygous | 127.2 +− 7.79 | 41.1 +− 11.11 | 16.8 +− 1.28 | 1.71 +− 0.28 *** |
| SR1 | no transgene | 147.6 +− 16.30 | 29 +− 4.6 | 17.8 +− 1.35 | 1.78 +− 0.13 *** |

* 95% interval of confidence
** three of five plants
*** Mean ± SD calculated from leaf 6 of five plants 74 days after sowing

TABLE 3

| | Line | | | | | |
|---|---|---|---|---|---|---|
| | 1.1 | 1.3 | 18.1 | 25 | 32 | SR1 |
| Number of flowers | 23.25 | 31.33 | 21.2 | 14 | 18.2 | 12.5 |

Example 8

Use of the Invention in Corn

The invention described herein can also be used in maize. To this aim, a cdc27a, for example a maize or other ortholog, is cloned under control of a constitutive promoter operable in maize, in a plant transformation vector suited for *Agrobacterium*-mediated corn transformation. Methods to use for corn transformation have been described in literature (Ishida et al., Nat Biotechnol. 1996 June; 14(6):745-50; Frame et al., Plant Physiol. 2002 May; 129(1):13-22). Transgenic plants made by these methods are grown in the greenhouse for T1 seed production. Inheritability and copy number of the transgene are checked by quantitative real-time PCR and Southern blot analysis and expression levels of the transgene are determined by reverse PCR and Northern analysis. Transgenic lines with single copy insertions of the transgene and with varying levels of transgene expression are selected for T2 seed production. Progeny seeds are germinated and grown in the greenhouse in conditions well adapted for maize (16:8 photoperiod, 26-28° C. daytime temperature and 22-24° C. nighttime temperature) as well under water-deficient, nitrogen-deficient, and excess NaCl conditions. Null segregants from the same parental line, as well as wild type plants of the same cultivar are used as controls. The progeny plants resulting from the selfing or the crosses are evaluated on different biomass and developmental parameters, including, stem size, number of leaves, total above ground area, leaf greenness, time to maturity, flowering time, time to flower, ear number, harvesting time. The seeds of these lines are also checked on various parameters, such as grain size, total grain yield per plant, and grain quality (starch content, protein content and oil content). Lines that are most significantly improved versus the controls for any of the above mentioned parameters are selected for further field testing and marker-assisted breeding, with the objective of transferring the field-validated transgenic traits into commercial germplasm. Methods for testing maize for growth and yield-related parameters in the field are well established in the art, as are techniques for introgressing specific loci (such as transgene containing loci) from one germplasm into another. Corn plants according to the present invention have changed development, changed rate of development changed organ formation, changed organ size and number, and/or changed reproductive characteristics, such as early flowering and increased number of flowers and seeds.

Example 9

Use of the Invention in Rice

The invention described herein can also be used in rice. To this aim, a cdc27a, for example a rice or other ortholog, is cloned under control of a constitutive promoter operable in rice, such as for example the GOS2 promoter, in a plant transformation vector suited for *Agrobacterium*-mediated transformation of rice. Such vectors and methods for rice transformation have been described in literature. The method yielded single locus transformants at a rate of over 50% are described in Aldemita and Hodges, Planta, 199 612-617, 1996; Chan et al., Plant Mol. Biol. 22 (3) 491-506, 1993, Hiei et al., Plant J., 6 (2) 271-282, 1994) or in EP1198985).

Transgenic plants generated by these rice transformation methods are evaluated for various developmental parameters. More particularly, the transgenic plants are evaluated and the following parameters are monitored: increased total above ground biomass, increased plant height, increased number of tillers, increased number of first panicles, increased number of second panicles, increased total number of seeds, increased number of filled seeds, increased total seed yield per plant, increased harvest index, increased thousand kernel weight, increased Tmid, increased T45 or A90, increased A42, changed cycling time or an changed growth curve, changed flowering time.

Plants with increase rate of development, increased organ formation, increase number and size of organs, reduces flowering time, more flowers and/or more seeds are selected with the objective of transferring the transgenic traits into commercial germplasm

The invention claimed is:

1. A method for modifying the development of a plant comprising:
transforming a plant cell with a nucleic acid encoding a CDC27A protein that is at least 95% homologous to SEQ ID NO: 2,
producing a plant or plant part from said transformed cell; and
selecting a plant or plant part that has at least one modified phenotype compared to a plant produced from a corresponding untransformed plant cell;
wherein said modified phenotype is selected from the group consisting of increased plant organ size, increased numbers of a plant organ, and earlier flowering, compared to a plant obtained from the corresponding untransformed plant cell.

2. The method according to claim 1, wherein said nucleic acid sequence encodes a polypeptide that is at least 99% homologous to SEQ ID NO: 2.

3. The method according to claim 1, wherein said nucleic acid sequence encodes a polypeptide comprising SEQ ID NO: 2.

4. The method according to claim 1, wherein said plant cell is transformed with a plasmid vector containing said nucleic acid sequence.

5. The method according to claim 1, wherein nucleic acid encoding a CDC27A protein is obtained from a dicotyledonous plant.

6. The method according to claim 1, wherein said nucleic acid sequence is introduced in a sense direction into a plant.

7. The method according to claim 1, wherein expression of said nucleic acid is driven by a constitutive promoter.

8. The method according to claim 1, wherein said modified phenotype is an increased plant organ size compared to a plant produced from a corresponding untransformed plant cell.

9. The method according to claim 8, wherein said plant organ is a leaf or a stem.

10. The method according to claim 1, wherein said modified phenotype is an increase in the numbers of at least one plant organ compared to a plant produced from a corresponding untransformed plant cell.

11. The method according to claim 1, wherein said modified phenotype is an increase in the numbers of leaves, flowers, or seeds compared to a plant produced from a corresponding untransformed plant cell.

12. The method of claim 1, wherein said nucleic acid sequence further comprises one or more non-native or non-endogenous control sequences that regulate the expression of said nucleic acid sequence in said transformed plant cell; and optionally, a transcription termination sequence.

13. The method according to claim 1, wherein said nucleic acid encoding a CDC27A protein that is at least 95% homologous to SEQ ID NO: 2 further comprises one or more control sequence(s) capable of regulating expression of the nucleic acid sequence of (i) in a plant; and/or
a transcription termination sequence.

14. A transgenic plant obtained by the method according to claim 1, or its transgenic progeny, wherein said plant or its transgenic progeny has a modified phenotype selected from the group consisting of increased plant organ size, increased numbers of a plant organ, and earlier flowering, compared to a plant obtained from the corresponding untransformed plant cell.

15. The plant of claim 14 having earlier flowering when compared to a plant obtained from the corresponding untransformed plant cell.

16. The plant according to claim 14,
wherein said plant is a monocotyledonous plant, and/or
wherein said plant is selected from rice, maize, wheat, barley, millet, soybean, leguminosae, rapeseed, sunflower, canola, alfalfa, sugarcane, popular, tobacco, and cotton.

17. A transgenic plant part or a propagule from a transgenic plant according to claim 14 or its progeny; wherein said transgenic plant part or propagule has a modified phenotype selected from the group consisting of increased plant organ size, increased numbers of a plant organ, and earlier flowering, compared to a plant obtained from the corresponding untransformed plant cell.

18. A plant or plant part comprising
a genetic construct that comprises
a nucleic acid sequence encoding a CDC27A protein that is at least 95% homologous to SEQ ID NO: 2;
one or more non-native or non-endogenous control sequences that regulate the expression of said nucleic acid sequence in a transformed plant cell; and optionally a transcription termination sequence,
wherein said plant or plant part has a modified phenotype selected from the group consisting of increased plant organ size, increased numbers of a plant organ, and earlier flowering, compared to a plant obtained from the corresponding untransformed plant cell.

19. A food product comprising the transgenic plant according to claim 14 or a transgenic part of said plant.

20. An animal feed or food comprising the transgenic plant according to claim 14 or a transgenic part of said plant.

21. The plant according to claim 18, wherein said plant is a monocotyledonous plant, and/or wherein said plant is selected from rice, maize, wheat, barley, millet, soybean, leguminosae, rapeseed, sunflower, canola, alfalfa, sugarcane, popular, tobacco, and cotton.

22. A transgenic plant part, a propagule or progeny obtained from the transgenic plant according to claim 18; wherein said plant part, propagule or progeny has a modified phenotype selected from the group consisting of increased plant organ size, increased numbers of a plant organ, and earlier flowering, compared to a plant obtained from the corresponding untransformed plant cell.

23. A method for modifying the development of a plant or a plant structure compared to an unmodified plant, comprising:
   transforming a plant cell with a polynucleotide encoding the polypeptide of SEQ ID NO: 2 or a sequence having at least 95% sequence identity with SEQ ID NO: 2, and
   cultivating a plant or plant part from said transformed cell,
   wherein said plant or plant part has increased plant organ size, increased numbers of a plant organ, or earlier flowering compared to a corresponding plant or plant part obtained from a corresponding untransformed plant cell.

24. The method of claim 23, further comprising selecting a plant which has accelerated development compared to a plant obtained from the corresponding untransformed wild-type plant.

25. The method of claim 23, further comprising selecting a plant which has a plant organ of increased size, an increased number of plant organs, or early flowering compared to a plant obtained from the corresponding untransformed wild-type plant.

* * * * *

SEQUENCE LISTING

<160> NUMBER OF SEQ ID NOS: 14

<210> SEQ ID NO 1
<211> LENGTH: 2434
<212> TYPE: DNA
<213> ORGANISM: Arabidopsis thaliana

```
<400> SEQUENCE: 1
atgatggaga atctactggc gaattgtgtc cagaaaaacc ttaaccattt tatgttcacc      60
aatgctatct tcctttgcga acttcttctc gcccaatttc catctgaggt gaacctgcaa     120
ttgttagcca ggtgttactt gagtaacagt caagcttata gtgcatatta tatccttaaa     180
ggttcaaaaa cgcctcagtc tcggtattta tttgcattct catgctttaa gttggatctt     240
cttggagagg ctgaagctgc attgttgccc tgtgaagatt atgctgaaga agttcctggt     300
ggtgcagctg gcattatctc tcttggtctt atatatagat attctgggag gaagaactgt     360
tcaatacaac agtttaggat ggcattgtca tttgatccat tgtgttggga agcatatgga     420
gaactttgta gtttaggtgc cgctgaagaa gcctcaacag ttttcgggaa tgttgcttcc     480
cagcgtctta aaacttgtgt agaacaaaga ataagcttct cagaaggagc aaccatagac     540
cagattacag attctgataa ggccttaaaa gatacaggtt atcgcaaac agaacacatt     600 ccaggagaga accaacaaga tctgaaaatt atgcagcagc ctggagatat tccaccaaat     660
actgacaggc aacttagtac aaacggatgg gacttgaaca caccttctcc agtgctttta     720
caggtaatgg atgctccacc gcctctgctt cttaagaata tgcgtcgtcc agcagtggaa     780
ggatctttga tgtctgtaca tggagtgcgt gtgcgtcgaa gaaactttt tagtgaagaa     840 ttgtcagcag aggctcaaga gaatctgggc gccgccgta gtgctagaat agcagcaagg     900
aaaaagaatc ctatgtcgca gtcatttgga aaagattccc attggttaca tctttcacct     960
tccgagtcaa actatgcacc ttctctttcc tcgatgattg gaaaatgcag aatccaaagc    1020
agcaaagaag cgattcctga taccgttact ctaaatgatc cagcaacgac gtcaggccag    1080
tctgtaagtg acactggaag ctctgttgat gatgaggaaa agtcaaatcc tagtgaatct    1140
tccccggatc gtttcagcct tatttctgga atttcagaag tgctaggcat tctgaaaatt    1200
cttggagatg gccacaggca tttacatatg tacaagtgtc aggaagcttt gttggcatat    1260
caaaagctat ctcagaaaca atacaataca cactgggttc tcatgcaggt tggaaaagca    1320
tattttgagc tacaagacta cttcaacgct gactcttcct ttactcttgc tcatcaaaag    1380
tatccttatg ctttggaagg aatggataca tactccactg ttctttatca cctgaaagaa    1440
gagatgaggt tgggctatct ggctcaggaa ctgatttcag ttgatcgcct gtctccagaa    1500
tcctggtgtg cagttgggaa ctgttacagt ttgcgtaagg atcatgatac tgctctcaaa    1560
atgtttcaga gagctatcca actgaatgaa agattcacat atgcacatac cctttgtggc    1620
cacgagtttg ccgcattgga agaattcgag gatgcagaga gatgctaccg gaaggctctg    1680
ggcatagata cgagacacta taatgcatgg tacggtcttg gaatgaccta tcttcgtcag    1740
gagaaattcg agtttgcgca gcatcaattt caactggctc tccaaataaa tccaagatct    1800
tcagtcatca tgtgttacta tggaattgct ttgcatgagt caaagagaaa cgatgaggcg    1860
ttgatgatga tggagaaggc tgtactcact gatgcaaaga atccgctccc caagtactac    1920
aaggctcaca tattaaccag cctaggtgat tatcacaaag cacagaaagt tttagaagag    1980
ctcaaagaat gtgctcctca agaaagcagt gtccatgcat cgcttggcaa aatatacaat    2040
cagctaaagc aatacgacaa agccgtgtta catttcggca ttgctttgga tttaagccct    2100
tctccatctg atgctgtcaa gataaaggct tacatggaga ggttgatact accagacgag    2160
ctggtgacgg aggaaaattt gtagatttat tgtgcaggta atacaccaga ttatgtttct    2220
catataaccc aaagtcatct gtaatttttc tcatctttag atcagtcttg tggactaacc    2280
ctaaaacaaa actgattata taaacttaga gggtaatatt acagaaaatt gtatagagtt    2340
```

```
gggtttgaat ttcatttct tttccaagtt ggaactttg ttcaaaaaaa aaaaaaaaaa      2400
aaaaaaaaaa aaaaaaaaaa aaaaaaaaaa aaaa                                2434
```

<210> SEQ ID NO 2
<211> LENGTH: 728
<212> TYPE: PRT
<213> ORGANISM: Arabidopsis thaliana

<400> SEQUENCE: 2

```
Met Met Glu Asn Leu Leu Ala Asn Cys Val Gln Lys Asn Leu Asn His
1               5                   10                  15

Phe Met Phe Thr Asn Ala Ile Phe Leu Cys Glu Leu Leu Leu Ala Gln
            20                  25                  30

Phe Pro Ser Glu Val Asn Leu Gln Leu Leu Ala Arg Cys Tyr Leu Ser
        35                  40                  45

Asn Ser Gln Ala Tyr Ser Ala Tyr Tyr Ile Leu Lys Gly Ser Lys Thr
50                  55                  60

Pro Gln Ser Arg Tyr Leu Phe Ala Phe Ser Cys Phe Lys Leu Asp Leu
65                  70                  75                  80

Leu Gly Glu Ala Glu Ala Ala Leu Leu Pro Cys Glu Asp Tyr Ala Glu
                85                  90                  95

Glu Val Pro Gly Gly Ala Ala Gly His Tyr Leu Leu Gly Leu Ile Tyr
            100                 105                 110

Arg Tyr Ser Gly Arg Lys Asn Cys Ser Ile Gln Gln Phe Arg Met Ala
        115                 120                 125

Leu Ser Phe Asp Pro Leu Cys Trp Glu Ala Tyr Gly Glu Leu Cys Ser
130                 135                 140

Leu Gly Ala Ala Glu Glu Ala Ser Thr Val Phe Gly Asn Val Ala Ser
145                 150                 155                 160

Gln Arg Leu Gln Lys Thr Cys Val Glu Gln Arg Ile Ser Phe Ser Glu
                165                 170                 175

Gly Ala Thr Ile Asp Gln Ile Thr Asp Ser Asp Lys Ala Leu Lys Asp
            180                 185                 190

Thr Gly Leu Ser Gln Thr Glu His Ile Pro Gly Glu Asn Gln Gln Asp
        195                 200                 205

Leu Lys Ile Met Gln Gln Pro Gly Asp Ile Pro Pro Asn Thr Asp Arg
210                 215                 220

Gln Leu Ser Thr Asn Gly Trp Asp Leu Asn Thr Pro Ser Pro Val Leu
225                 230                 235                 240

Leu Gln Val Met Asp Ala Leu Pro Pro Leu Leu Lys Asn Met Arg
                245                 250                 255

Arg Pro Ala Val Glu Gly Ser Leu Met Ser Val His Gly Val Arg Val
            260                 265                 270

Arg Arg Arg Asn Phe Phe Ser Glu Glu Leu Ser Ala Glu Ala Gln Glu
        275                 280                 285

Glu Ser Gly Arg Arg Arg Ser Ala Arg Ile Ala Ala Arg Lys Lys Asn
    290                 295                 300

Pro Met Ser Gln Ser Phe Gly Lys Asp Ser His Trp Leu His Leu Ser
305                 310                 315                 320

Pro Ser Glu Ser Asn Tyr Ala Pro Ser Leu Ser Ser Met Ile Gly Lys
                325                 330                 335

Cys Arg Ile Gln Ser Ser Lys Glu Val Ile Pro Asp Thr Val Thr Leu
            340                 345                 350

Asn Asp Pro Ala Thr Thr Ser Gly Gln Ser Val Ser Asp Ile Gly Ser
```

```
            355                 360                 365
Ser Val Asp Asp Glu Glu Lys Ser Asn Pro Ser Glu Ser Ser Pro Asp
370                 375                 380

Arg Phe Ser Leu Ile Ser Gly Ile Ser Glu Val Leu Ser Leu Leu Lys
385                 390                 395                 400

Ile Leu Gly Asp Gly His Arg His Leu His Met Tyr Lys Cys Gln Glu
                405                 410                 415

Ala Leu Leu Ala Tyr Gln Lys Leu Ser Gln Lys Gln Tyr Asn Thr His
                420                 425                 430

Trp Val Leu Met Gln Val Gly Lys Ala Tyr Phe Glu Leu Gln Asp Tyr
                435                 440                 445

Phe Asn Ala Asp Ser Ser Phe Thr Leu Ala His Gln Lys Tyr Pro Tyr
450                 455                 460

Ala Leu Glu Gly Met Asp Thr Tyr Ser Thr Val Leu Tyr His Leu Lys
465                 470                 475                 480

Glu Glu Met Arg Leu Gly Tyr Leu Ala Gln Glu Leu Ile Ser Val Asp
                485                 490                 495

Arg Leu Ser Pro Glu Ser Trp Cys Ala Val Gly Asn Cys Tyr Ser Leu
                500                 505                 510

Arg Lys Asp His Asp Thr Ala Leu Lys Met Phe Gln Arg Ala Ile Gln
                515                 520                 525

Leu Asn Glu Arg Phe Thr Tyr Ala His Thr Leu Cys Gly His Glu Phe
530                 535                 540

Ala Ala Leu Glu Glu Phe Glu Asp Ala Glu Arg Cys Tyr Arg Lys Ala
545                 550                 555                 560

Leu Gly Ile Asp Thr Arg His Tyr Asn Ala Trp Tyr Gly Leu Gly Met
                565                 570                 575

Thr Tyr Leu Arg Gln Glu Lys Phe Glu Phe Ala Gln His Gln Phe Gln
                580                 585                 590

Leu Ala Leu Gln Ile Asn Pro Arg Ser Ser Val Ile Met Cys Tyr Tyr
                595                 600                 605

Gly Ile Ala Leu His Glu Ser Lys Arg Asn Asp Glu Ala Leu Met Met
610                 615                 620

Met Glu Lys Ala Val Leu Thr Asp Ala Lys Asn Pro Leu Pro Lys Tyr
625                 630                 635                 640

Tyr Lys Ala His Ile Leu Thr Ser Leu Gly Asp Tyr His Lys Ala Gln
                645                 650                 655

Lys Val Leu Glu Glu Leu Lys Glu Cys Ala Pro Gln Glu Ser Ser Val
                660                 665                 670

His Ala Ser Leu Gly Lys Ile Tyr Asn Gln Leu Lys Gln Tyr Asp Lys
                675                 680                 685

Ala Val Leu His Phe Gly Ile Ala Leu Asp Leu Ser Pro Ser Pro Ser
                690                 695                 700

Asp Ala Val Lys Ile Lys Ala Tyr Met Glu Arg Leu Ile Leu Pro Asp
705                 710                 715                 720

Glu Leu Val Thr Glu Glu Asn Leu
                725

<210> SEQ ID NO 3
<211> LENGTH: 2401
<212> TYPE: DNA
<213> ORGANISM: Arabidopsis thaliana

<400> SEQUENCE: 3
atgatggaga atctactggc gaattgtgtc cagaaaaacc ttaaccattt tatgttcacc      60
```

```
aatgctatct tcctttgcga acttcttctc gcccaatttc catctgaggt gaacctgcaa    120
ttgttagcca ggtgttactt gagtaacagt caagcttata gtgcatatta tatccttaaa    180
ggttcaaaaa cgcctcagtc tcggtattta tttgcattct catgctttaa gttggatctt    240
cttggagagg ctgaagctgc attgttgccc tgtgaagatt atgctgaaga agttcctggt    300
ggtgcagctg ggcattatct tcttggtctt atatatagat attctgggag gaagaactgt    360
tcaatacaac agtttaggat ggcattgtca tttgatccat tgtgttggga agcatatgga    420
gaactttgta gtttaggtgc cgctgaagaa gcctcaacag ttttcgggaa tgttgcttcc    480
cagcgtctta aaacttgtgt agaacaaaga ataagcttct cagaaggagc aaccatagac    540
cagattacag attctgataa ggccttaaaa gatacaggtt tatcgcaaac agaacacatt    600
ccaggagaga accaacaaga tctgaaaatt atgcagcagc ctggagatat tccaccaaat    660
actgacaggc aacttagtac aaacggatgg gacttgaaca caccttctcc agtgctttta    720
caggtaatgg atgctccacc gcctctgctt cttaagaata tgcgtcgtcc agcagtggaa    780
ggatctttga tgtctgtaca tggagtgcgt gtgcgtcgaa gaaacttttt tagtgaagaa    840
ttgtcagcag aggctcaaga agaatctggg cgccgccgta gtgctagaat agcagcaagg    900
aaaaagaatc ctatgtcgca gtcatttgga aaagattccc attggttaca tctttcacct    960
tccgagtcaa actatgcacc ttctctttcc tcgatgattg aaaatgcag aatccaaagc   1020 agcaaagaag caacgacgtc aggccagtct gtaagtgaca ctggaagctc tgttgatgat   1080
gaggaaaagt caaatcctag tgaatcttcc ccggatcgtt tcagcccttat ttctggaatt   1140 tcagaagtgc taagcattct gaaaattctt ggagatggcc acaggcattt acatatgtac   1200
aagtgtcagg aagcttttgtt ggcatatcaa aagctatctc agaaacaata caatacacac   1260
tgggttctca tgcaggttgg aaaagcatat tttgagctac aagactactt caacgctgac   1320 tcttcccttta ctcttgctca tcaaaagtat ccttatgctt tggaaggaat ggatacatac   1380
tccactgttc tttatcacct gaaagaagag atgaggttgg gctatctggc tcaggaactg   1440
atttcagttg atcgcctgtc tccagaatcc tggtgtgcag ttgggaactg ttacagtttg   1500
cgtaaggatc atgatactgc tctcaaaatg tttcagagag ctatccaact gaatgaaaga   1560
ttcacatatg cacataccct ttgtggccac gagtttgccg cattggaaga attcgaggat   1620
gcagagagat gctaccggaa ggctctgggc atagatacga gacactataa tgcatggtac   1680
ggtcttggaa tgacctatct tcgtcaggag aaattcgagt ttgcgcagca tcaatttcaa   1740
ctggctctcc aaataaatcc aagatcttca gtcatcatgt gttactatgg aattgctttg   1800
catgagtcaa agagaaacga tgaggcgttg atgatgatgg agaaggctgt actcactgat   1860
gcaaagaatc cgctccccaa gtactacaag gctcacatat taaccagcct aggtgattat   1920
cacaaagcac agaaagtttt agaagagctc aagaatgtg ctcctcaaga aagcagtgtc   1980
catgcatcgc ttggcaaaat atacaatcag ctaaagcaat acgacaaagc cgtgttacat   2040
ttcggcattg ctttggattt aagcccttct ccatctgatg ctgtcaagat aaaggcttac   2100
atggagaggt tgatactacc agacgagctg gtgacggagg aaaatttgta gatttattgt   2160
gcaggtaata caccagatta tgtttctcat ataacccaaa gtcatctgta attttttctca   2220 tctttagatc agtcttgtgg actaacccta aaacaaaact gattatataa acttagaggg   2280
taatattaca gaaaattgta tagagttggg tttgaatttt catttctttt ccaagttgga   2340
acttttgttc aaaaaaaaaa aaaaaaaaaa aaaaaaaaaa aaaaaaaaaa aaaaaaaaaa   2400
a                                                                  2401
```

<210> SEQ ID NO 4
<211> LENGTH: 716
<212> TYPE: PRT
<213> ORGANISM: Arabidopsis thaliana

<400> SEQUENCE: 4

```
Met Met Glu Asn Leu Leu Ala Asn Cys Val Gln Lys Asn Leu Asn His
1               5                   10                  15

Phe Met Phe Thr Asn Ala Ile Phe Leu Cys Glu Leu Leu Leu Ala Gln
            20                  25                  30

Phe Pro Ser Glu Val Asn Leu Gln Leu Leu Ala Arg Cys Tyr Leu Ser
        35                  40                  45

Asn Ser Gln Ala Tyr Ser Ala Tyr Tyr Ile Leu Lys Gly Ser Lys Thr
    50                  55                  60

Pro Gln Ser Arg Tyr Leu Phe Ala Phe Ser Cys Phe Lys Leu Asp Leu
65                  70                  75                  80

Leu Gly Glu Ala Glu Ala Ala Leu Leu Pro Cys Glu Asp Tyr Ala Glu
                85                  90                  95

Glu Val Pro Gly Gly Ala Gly His Tyr Leu Leu Gly Leu Ile Tyr
            100                 105                 110

Arg Tyr Ser Gly Arg Lys Asn Cys Ser Ile Gln Gln Phe Arg Met Ala
        115                 120                 125

Leu Ser Phe Asp Pro Leu Cys Trp Glu Ala Tyr Gly Glu Leu Cys Ser
130                 135                 140

Leu Gly Ala Ala Glu Glu Ala Ser Thr Val Phe Gly Asn Val Ala Ser
145                 150                 155                 160

Gln Arg Leu Lys Thr Cys Val Glu Gln Arg Ile Ser Phe Ser Glu Gly
                165                 170                 175

Ala Thr Ile Asp Gln Ile Thr Asp Ser Asp Lys Ala Leu Lys Asp Thr
            180                 185                 190

Gly Leu Ser Gln Thr Glu His Ile Pro Gly Glu Asn Gln Gln Asp Leu
        195                 200                 205

Lys Ile Met Gln Gln Pro Gly Asp Ile Pro Pro Asn Thr Asp Arg Gln
    210                 215                 220

Leu Ser Thr Asn Gly Trp Asp Leu Asn Thr Pro Ser Pro Val Leu Leu
225                 230                 235                 240

Gln Val Met Asp Ala Pro Pro Leu Leu Leu Lys Asn Met Arg Arg
                245                 250                 255

Pro Ala Val Glu Gly Ser Leu Met Ser Val His Gly Val Arg Val Arg
            260                 265                 270

Arg Arg Asn Phe Phe Ser Glu Glu Leu Ser Ala Glu Ala Gln Glu Glu
        275                 280                 285

Ser Gly Arg Arg Arg Ser Ala Arg Ile Ala Ala Arg Lys Lys Asn Pro
    290                 295                 300

Met Ser Gln Ser Phe Gly Lys Asp Ser His Trp Leu His Leu Ser Pro
305                 310                 315                 320

Ser Glu Ser Asn Tyr Ala Pro Ser Leu Ser Ser Met Ile Gly Lys Cys
                325                 330                 335

Arg Ile Gln Ser Ser Lys Glu Ala Thr Thr Ser Gly Gln Ser Val Ser
            340                 345                 350

Asp Thr Gly Ser Ser Val Asp Asp Glu Glu Lys Ser Asn Pro Ser Glu
        355                 360                 365

Ser Ser Pro Asp Arg Phe Ser Leu Ile Ser Gly Ile Ser Glu Val Leu
    370                 375                 380
```

```
Ser Ile Leu Lys Ile Leu Gly Asp Gly His Arg His Leu His Met Tyr
385                 390                 395                 400

Lys Cys Gln Glu Ala Leu Leu Ala Tyr Gln Lys Leu Ser Gln Lys Gln
            405                 410                 415

Tyr Asn Thr His Trp Val Leu Met Gln Val Gly Lys Ala Tyr Phe Glu
            420                 425                 430

Leu Gln Asp Tyr Phe Asn Ala Asp Ser Ser Phe Thr Leu Ala His Gln
            435                 440                 445

Lys Tyr Pro Tyr Ala Leu Glu Gly Met Asp Tyr Ser Thr Val Leu
            450                 455                 460

Tyr His Leu Lys Glu Glu Met Arg Leu Gly Tyr Leu Ala Gln Glu Leu
465                 470                 475                 480

Ile Ser Val Asp Arg Leu Ser Pro Glu Ser Trp Cys Ala Val Gly Asn
            485                 490                 495

Cys Tyr Ser Leu Arg Lys Asp His Asp Thr Ala Leu Lys Met Phe Gln
            500                 505                 510

Arg Ala Ile Gln Leu Asn Glu Arg Phe Thr Tyr Ala His Thr Leu Cys
            515                 520                 525

Gly His Glu Phe Ala Ala Leu Glu Glu Phe Glu Asp Ala Glu Arg Cys
            530                 535                 540

Tyr Arg Lys Ala Leu Gly Ile Asp Thr Arg His Tyr Asn Ala Trp Tyr
545                 550                 555                 560

Gly Leu Gly Met Thr Tyr Leu Arg Gln Glu Lys Phe Glu Phe Ala Gln
            565                 570                 575

His Gln Phe Gln Leu Ala Leu Gln Ile Asn Pro Arg Ser Ser Val Ile
            580                 585                 590

Met Cys Tyr Tyr Gly Ile Ala Leu His Glu Ser Lys Arg Asn Asp Glu
            595                 600                 605

Ala Leu Met Met Met Glu Lys Ala Val Leu Thr Asp Ala Lys Asn Pro
610                 615                 620

Leu Pro Lys Tyr Tyr Lys Ala His Ile Leu Thr Ser Leu Gly Asp Tyr
625                 630                 635                 640

His Lys Ala Gln Lys Val Leu Glu Glu Leu Lys Glu Cys Ala Pro Gln
            645                 650                 655

Glu Ser Ser Val His Ala Ser Leu Gly Lys Ile Tyr Asn Gln Leu Lys
            660                 665                 670

Gln Tyr Asp Lys Ala Val Leu His Phe Gly Ile Ala Leu Asp Leu Ser
            675                 680                 685

Pro Ser Pro Ser Asp Ala Val Lys Ile Lys Ala Tyr Met Glu Arg Leu
            690                 695                 700

Ile Leu Pro Asp Glu Leu Val Thr Glu Glu Asn Leu
705                 710                 715

<210> SEQ ID NO 5
<211> LENGTH: 1892
<212> TYPE: DNA
<213> ORGANISM: Oryza sativa
<220> FEATURE:
<221> NAME/KEY: misc_feature
<222> LOCATION: (730)..(734)
<223> OTHER INFORMATION: n is a, t, g or c

<400> SEQUENCE: 5
atggaaaccc taatggtgga ccgcgtccac ggcagcctcc gcctcttcat gcaccgcaac      60
gccgtcttcc tctgcgagcg cctctgcgcc cagttccccg ccgagacaaa tgtccagttg     120
```

```
ctagcaactt gctaccttca caacaaccag ccatatgctg cataccacat cttgaaagga    180
aagaagctgc cagagtcccg gtacttgttt gctatgtcat gcttccgaat gaacctctta    240
cgggaagctg aagaagcctt gtgtcctgtc aatgaaccaa atattgaggt tccaagtggt    300
gcaacagggc actaccttct tggagtaatt tacaggtaca ctggcagagt ggaagctgca    360
gctgagcaat ttgtacaagc tctgactctt gatcctcttc tatgggcagc atacgaggaa    420
ttgtgcatac taggtgttgc tgaagatgca atgaatgtt tcagtgaagc aacagctcta    480
cgtcttcagc aggaactcac atccacatca aatgtggaaa agtcaaactt gttaatgaa     540
aatcggtttc tatcttccaa tgtgtcagca agttttggtg atagtcctaa gcaaattaaa    600
cagctgcatg ctaacaccac tgcagaagta tctggttatc ctcatgtaaa gtcaactgca    660
ttgcatatgc agaacggtgc accatctaat ttatcacagt ttgacactcc atcgccaact    720
tcaacgcagn nnnataatgt aacttcaact tcgtcttcta caagtatagt tgatggaaga    780
tatcccgagc aagagaaatc tgaacgagtt ctgtcacagg actccaaatt agctattggt    840
atcagggagc taatggcact cttgcggaca ctaggggaag ggtataggct ttcttgcttg    900
tttaagtgtc aggaagcatt ggaagtatat agaaagctcc cagaggcaca atttaatact    960
ggatgggttc tttgccaggt tgggaagaca tattttgaac tcgtcaatta tttagaagcc   1020
gatcattttt ttgagttagc gcatcgacta tcaccatgca cgttggaggg aatggacatt   1080
tactccactg ttctttatca tttgaatgag gaaatgcggc taagttacct tgctcaagat   1140
cttgttccta ttgatcgact atctccccaa gcatggtgtg ctgtgggaaa ttgctttgcc   1200
ttgaggaaag atcatgagac tgccttgaag aattttcaac gtgctgtaca gcttgactca   1260
agagttgcat acgctcacac gctatgcggt cacgatataa aactataccg atctgcactt   1320
caggtagatg aaagacacta caatgcctgg tatggccttg gagtggtgta ccttcgccag   1380
gaaaagtttg agtttgctga gcatcatttc agaagggcat tccagataaa tccttgctct   1440
tctgttctta tgtgctatct tgggatggcc ttgcatgctt taaagaggaa tgaggaagcc   1500
ttggaaatga tggagaaggc tatatttgct gataagaaga atccactccc caagtatcaa   1560
aaggctttaa tccttctagg cctacaaaaa taccctgatg ctctggatga gttggaacgg   1620
ctaaaggaaa ttgcacctca tgaaagtagt atgtatgcac tgatgggaaa gatttacaag   1680
caacttaaca ttcttgacaa ggctgtattt tgctttggca ttgccctgga tttgaaacct   1740
cctgctgctg acgttgctat aatacaatct gcaatggaga agtacaccct tccagatgaa   1800
cttatggatg atgatgatga tgatgatgag atttaagctc actccgaaga acagagggga   1860
ggaaccaaca ttgattggca tgcctgtgct tg                                  1892
```

<210> SEQ ID NO 6
<211> LENGTH: 611
<212> TYPE: PRT
<213> ORGANISM: Oryza sativa
<220> FEATURE:
<221> NAME/KEY: MISC_FEATURE
<222> LOCATION: (244)..(245)
<223> OTHER INFORMATION: Xaa is any amino acid

<400> SEQUENCE: 6

Met Glu Thr Leu Met Val Asp Arg Val His Gly Ser Leu Arg Leu Phe
1               5                   10                  15

Met His Arg Asn Ala Val Phe Leu Cys Glu Arg Leu Cys Ala Gln Phe
            20                  25                  30

Pro Ala Glu Thr Asn Val Gln Leu Leu Ala Thr Cys Tyr Leu His Asn
        35                  40                  45

```
Asn Gln Pro Tyr Ala Ala Tyr His Ile Leu Lys Gly Lys Lys Leu Pro
    50                  55                  60

Glu Ser Arg Tyr Leu Phe Ala Met Ser Cys Phe Arg Met Asn Leu Leu
65                  70                  75                  80

Arg Glu Ala Glu Glu Ala Leu Cys Pro Val Asn Glu Pro Asn Ile Glu
                85                  90                  95

Val Pro Ser Gly Ala Thr Gly His Tyr Leu Leu Gly Val Ile Tyr Arg
            100                 105                 110

Tyr Thr Gly Arg Val Glu Ala Ala Glu Gln Phe Val Gln Ala Leu
            115                 120                 125

Thr Leu Asp Pro Leu Leu Trp Ala Ala Tyr Glu Glu Leu Cys Ile Leu
    130                 135                 140

Gly Val Ala Glu Asp Ala Asn Glu Cys Phe Ser Glu Ala Thr Ala Leu
145                 150                 155                 160

Arg Leu Gln Gln Glu Leu Thr Ser Thr Ser Asn Val Glu Lys Ser Asn
                165                 170                 175

Phe Val Asn Glu Asn Arg Phe Leu Ser Ser Asn Val Ser Ala Ser Phe
            180                 185                 190

Gly Asp Ser Pro Lys Gln Ile Lys Gln Leu His Ala Asn Thr Thr Ala
            195                 200                 205

Glu Val Ser Gly Tyr Pro His Val Lys Ser Thr Ala Leu His Met Gln
210                 215                 220

Asn Gly Ala Pro Ser Asn Leu Ser Gln Phe Asp Thr Pro Ser Pro Thr
225                 230                 235                 240

Ser Thr Gln Xaa Xaa Asn Val Thr Ser Thr Ser Ser Thr Ser Ile
                245                 250                 255

Val Asp Gly Arg Tyr Pro Glu Gln Glu Lys Ser Glu Arg Val Leu Ser
            260                 265                 270

Gln Asp Ser Lys Leu Ala Ile Gly Ile Arg Glu Leu Met Ala Leu Leu
            275                 280                 285

Arg Thr Leu Gly Glu Gly Tyr Arg Leu Ser Cys Leu Phe Lys Cys Gln
    290                 295                 300

Glu Ala Leu Glu Val Tyr Arg Lys Leu Pro Glu Ala Gln Phe Asn Thr
305                 310                 315                 320

Gly Trp Val Leu Cys Gln Val Gly Lys Thr Tyr Phe Glu Leu Val Asn
                325                 330                 335

Tyr Leu Glu Ala Asp His Phe Phe Glu Leu Ala His Arg Leu Ser Pro
            340                 345                 350

Cys Thr Leu Glu Gly Met Asp Ile Tyr Ser Thr Val Leu Tyr His Leu
    355                 360                 365

Asn Glu Glu Met Arg Leu Ser Tyr Leu Ala Gln Asp Leu Val Ser Ile
370                 375                 380

Asp Arg Leu Ser Pro Gln Ala Trp Cys Ala Val Gly Asn Cys Phe Ala
385                 390                 395                 400

Leu Arg Lys Asp His Glu Thr Ala Leu Lys Asn Phe Gln Arg Ala Val
                405                 410                 415

Gln Leu Asp Ser Arg Val Ala Tyr Ala His Thr Leu Cys Gly His Asp
            420                 425                 430

Ile Lys Leu Tyr Arg Ser Ala Leu Gln Val Asp Glu Arg His Tyr Asn
            435                 440                 445

Ala Trp Tyr Gly Leu Gly Val Val Tyr Leu Arg Gln Glu Lys Phe Glu
450                 455                 460

Phe Ala Glu His His Phe Arg Arg Ala Phe Gln Ile Asn Pro Cys Ser
```

```
                465                 470                 475                 480
Ser Val Leu Met Cys Tyr Leu Gly Met Ala Leu His Ala Leu Lys Arg
                    485                 490                 495
Asn Glu Glu Ala Leu Glu Met Met Glu Lys Ala Ile Phe Ala Asp Lys
                500                 505                 510
Lys Asn Pro Leu Pro Lys Tyr Gln Lys Ala Leu Ile Leu Leu Gly Leu
            515                 520                 525
Gln Lys Tyr Pro Asp Ala Leu Asp Glu Leu Glu Arg Leu Lys Glu Ile
        530                 535                 540
Ala Pro His Glu Ser Ser Met Tyr Ala Leu Met Gly Lys Ile Tyr Lys
545                 550                 555                 560
Gln Leu Asn Ile Leu Asp Lys Ala Val Phe Cys Phe Gly Ile Ala Leu
                565                 570                 575
Asp Leu Lys Pro Pro Ala Ala Asp Val Ala Ile Ile Gln Ser Ala Met
                580                 585                 590
Glu Lys Val His Leu Pro Asp Glu Leu Met Asp Asp Asp Asp Asp
            595                 600                 605
Asp Glu Ile
    610

<210> SEQ ID NO 7
<211> LENGTH: 2559
<212> TYPE: DNA
<213> ORGANISM: Saccharum sp.
<220> FEATURE:
<221> NAME/KEY: misc_feature
<222> LOCATION: (911)..(911)
<223> OTHER INFORMATION: n is a, t, g or c
<220> FEATURE:
<221> NAME/KEY: misc_feature
<222> LOCATION: (1327)..(1327)
<223> OTHER INFORMATION: n is a, t, g or c
<220> FEATURE:
<221> NAME/KEY: misc_feature
<222> LOCATION: (1792)..(1792)
<223> OTHER INFORMATION: n is a, t, g or c

<400> SEQUENCE: 7
ggtcgaccca cgcgtccgac cggaccctcc cactgctgcg cctgccgcct gcgcttcggc      60
caccgcacaa cacttcccct cgctctcgcc cgcccgcccg cgctcgccgc cgccgccgcc     120
gccgggcgga gatggaaacc ctaatggtgg accgcgtcca cagcagcctc cgcctcttca     180
tgcaccgcaa cgccgtattc ctctgcgagc gcctctgcgc gcagttcccc tccgagacca     240
atgtgcaatt gttagcgacc tgctacctcc acaacaatca gccatatgct cataccaca     300 ttttgaaagg gaagaagctg ccggagtccc ggtacttgtt tgctacatca tgctttcgaa     360
tgaacctctt gcgtgaagca gaagaaactc tatgtccagt caatgaacca acatggagg     420 ttccaagtgg agcaacagga cactacctcc ttggagtgat ttacaggtgc acaggcagaa     480
tttcagctgc agctgaacaa tttacacaag cgttgactct agatcctctt ttatgggcgg     540
catatgagga attgtgtata ttaggtattg ctgaagatac tgatgagtgt tttagtgaat     600
cgactgctct acgtctccag caggaacaca catccacggc cactctggtg aagtcgaact     660
tcgccaatga aaatcgagtt ctatcatcca gggtctctgc aaatcttggg gatattagtc     720
ctaagcaaat caaacagctt catgctaaca acatagcaga agtatctggc tatcctcatg     780
taagaccaac tgcattgcat gtgcagaaca gttcaacctc taatgtagca cagtttgaca     840
ccccatcacc aactgcagca cagacttcta gtatcatgcc accaccactc tttaggaatg     900
tccatgctta nattcaaatt caaatacctg gggtttggag ggaatggtac aggttattcg     960
```

```
tcagggaaat tgcgagtaaa ctcgtccaca ccatcaaaat ggtgttaacc accatacgtt    1020
ccgtgcaagt taggaaagga aaaccacggg ctacagaaaa ttttgatgaa ggaagtagat    1080
atgaagtcat tgatgaaatg tggacagaca atatatcagg aacttcatct tctgtaagta    1140
cagctgatgg aagatccttt gagcaagata aagctgaacg aattctgttg caagactcca    1200
aattggcact tggtattagg gagatattgg gacttgtccg aacactcggt gaaggttgta    1260
ggctttcttg cttgtttaag tgccatgaag ccttggaagt ctacagaaga ctccctgaga    1320
cccattntag cactgatgg agcatatgcc aggttggtaa ggcatatttc gaattagttg     1380
attatttgga agctgatcgt tactttgaat tggcacaccg actgtcgcct tgtacgcttg    1440
atggaatgga catctattct actgttcttt atcatctgaa tgaggaaatg agactaagct    1500
accttgctca agagcttatt tccattgatc gactatctcc tcaagcatgg tgtgcagtgg    1560
gcaattgctt tgccttgagg aaagatcatg agactgcttt gaagaatttt caacgttcgg    1620
tacagcttga ctcaagattt gcatatgctc acactctatg tggtcatgag tattctgcat    1680
tggaggatta tgagaatagt atcaaattct accggtgtgc actgcaggta gatgaaaggc    1740
actacaatgc ctggtatggc cttggggtgg tgtatcttcg ccaggaaaag tntgagtttg    1800
ctgagcatca tttcagaagg gcatttcaga taaatcctcg ctcttctgtt ctcatgtgct    1860
atcttgggat ggcgttgcat tctcttaaga ggaaggagga ggcattggaa atgatggaga    1920
aagctatagc agctgataag aagaatccac tgcccaagta tcagaaggcc ttaatccttc    1980
taggtcttca gaagtatcaa gaagctctgg atgagttgga gcggctaaag gagattgcac    2040
ctcatgagag cagtatgtat gcactgatgg gaaagattta caagcaactc aatatccttg    2100
acaaagctgt tttctgcttt ggcattgccc tggatttgaa acctcctgct gctgatcttg    2160
ctataattaa gtccgcaatg gagaaagtac atctccctga tgaactgatg gaggatgacc    2220
tgtaagttcg ctcaagcaca gtgagaaagg aacatttact tcgggtccat gatgctttgc    2280
ttgtgcttcg tgttcctggc ctgcttaggc ttctcaagtg gaactcagat cttggagctg    2340
taccatcaac catccagttt tgtagattta gttgtagcct ataatcagag aacacatgcg    2400
cagaagctgc agtagtttag gactctgtac aagttgagcg ttggcaaaat gacgcctgta    2460
ccattataca gttgtgatat taacaaaaca catccttgtc aaataacgga aataatcaaa    2520
ggatgaggat cctgctgatt caagcagatt gtttgtcgc                           2559
```

<210> SEQ ID NO 8
<211> LENGTH: 697
<212> TYPE: PRT
<213> ORGANISM: Saccharum sp.
<220> FEATURE:
<221> NAME/KEY: MISC_FEATURE
<222> LOCATION: (260)..(260)
<223> OTHER INFORMATION: Xaa is any amino acid
<220> FEATURE:
<221> NAME/KEY: MISC_FEATURE
<222> LOCATION: (399)..(399)
<223> OTHER INFORMATION: Xaa is any amino acid
<220> FEATURE:
<221> NAME/KEY: MISC_FEATURE
<222> LOCATION: (554)..(554)
<223> OTHER INFORMATION: Xaa is any amino acid

<400> SEQUENCE: 8

```
Met Glu Thr Leu Met Val Asp Arg Val His Ser Ser Leu Arg Leu Phe
 1               5                  10                  15

Met His Arg Asn Ala Val Phe Leu Cys Glu Arg Leu Cys Ala Gln Phe
            20                  25                  30
```

```
Pro Ser Glu Thr Asn Val Gln Leu Leu Ala Thr Cys Tyr Leu His Asn
        35                  40                  45

Asn Gln Pro Tyr Ala Ala Tyr His Ile Leu Lys Gly Lys Lys Leu Pro
50                  55                  60

Glu Ser Arg Tyr Leu Phe Ala Thr Ser Cys Phe Arg Met Asn Leu Leu
65                  70                  75                  80

Arg Glu Ala Glu Glu Thr Leu Cys Pro Val Asn Glu Pro Asn Met Glu
                85                  90                  95

Val Pro Ser Gly Ala Thr Gly His Tyr Leu Leu Gly Val Ile Tyr Arg
                100                 105                 110

Cys Thr Gly Arg Ile Ser Ala Ala Glu Gln Phe Thr Gln Ala Leu
            115                 120                 125

Thr Leu Asp Pro Leu Leu Trp Ala Ala Tyr Glu Glu Leu Cys Ile Leu
        130                 135                 140

Gly Ile Ala Glu Asp Thr Asp Glu Cys Phe Ser Glu Ser Thr Ala Leu
145                 150                 155                 160

Arg Leu Gln Gln Glu His Thr Ser Thr Ala Thr Leu Val Lys Ser Asn
                165                 170                 175

Phe Ala Asn Glu Asn Arg Val Leu Ser Ser Arg Val Ser Ala Asn Leu
                180                 185                 190

Gly Asp Ile Ser Pro Lys Gln Ile Lys Gln Leu His Ala Asn Asn Ile
            195                 200                 205

Ala Glu Val Ser Gly Tyr Pro His Val Arg Pro Thr Ala Leu His Val
        210                 215                 220

Gln Asn Ser Ser Thr Ser Asn Val Ala Gln Phe Asp Thr Pro Ser Pro
225                 230                 235                 240

Thr Ala Ala Gln Thr Ser Ser Ile Met Pro Pro Leu Phe Arg Asn
                245                 250                 255

Val His Ala Xaa Ile Gln Ile Gln Ile Pro Gly Val Trp Arg Glu Trp
                260                 265                 270

Tyr Arg Leu Phe Val Arg Glu Ile Ala Ser Lys Leu Val His Thr Ile
        275                 280                 285

Lys Met Val Leu Thr Thr Ile Arg Ser Val Gln Val Arg Lys Gly Lys
        290                 295                 300

Pro Arg Ala Thr Glu Asn Phe Asp Glu Gly Ser Arg Tyr Glu Val Ile
305                 310                 315                 320

Asp Glu Met Trp Thr Asp Asn Ile Ser Gly Thr Ser Ser Val Ser
                325                 330                 335

Thr Ala Asp Gly Arg Ser Phe Glu Gln Asp Lys Ala Glu Arg Ile Leu
                340                 345                 350

Leu Gln Asp Ser Lys Leu Ala Leu Gly Ile Arg Glu Ile Leu Gly Leu
            355                 360                 365

Val Arg Thr Leu Gly Glu Gly Cys Arg Leu Ser Cys Leu Phe Lys Cys
        370                 375                 380

His Glu Ala Leu Glu Val Tyr Arg Arg Leu Pro Glu Thr His Xaa Ser
385                 390                 395                 400

Thr Gly Trp Ser Ile Cys Gln Val Gly Lys Ala Tyr Phe Glu Leu Val
                405                 410                 415

Asp Tyr Leu Glu Ala Asp Arg Tyr Phe Glu Leu Ala His Arg Leu Ser
            420                 425                 430

Pro Cys Thr Leu Asp Gly Met Asp Ile Tyr Ser Thr Val Leu Tyr His
        435                 440                 445

Leu Asn Glu Glu Met Arg Leu Ser Tyr Leu Ala Gln Glu Leu Ile Ser
```

```
                450                 455                 460
Ile Asp Arg Leu Ser Pro Gln Ala Trp Cys Ala Val Gly Asn Cys Phe
465                 470                 475                 480

Ala Leu Arg Lys Asp His Glu Thr Ala Leu Lys Asn Phe Gln Arg Ser
                485                 490                 495

Val Gln Leu Asp Ser Arg Phe Ala Tyr Ala His Thr Leu Cys Gly His
                500                 505                 510

Glu Tyr Ser Ala Leu Glu Asp Tyr Glu Asn Ser Ile Lys Phe Tyr Arg
                515                 520                 525

Cys Ala Leu Gln Val Asp Glu Arg His Tyr Asn Ala Trp Tyr Gly Leu
530                 535                 540

Gly Val Val Tyr Leu Arg Gln Glu Lys Xaa Glu Phe Ala Glu His His
545                 550                 555                 560

Phe Arg Arg Ala Phe Gln Ile Asn Pro Arg Ser Ser Val Leu Met Cys
                565                 570                 575

Tyr Leu Gly Met Ala Leu His Ser Leu Lys Arg Lys Glu Glu Ala Leu
                580                 585                 590

Glu Met Met Glu Lys Ala Ile Ala Ala Asp Lys Lys Asn Pro Leu Pro
                595                 600                 605

Lys Tyr Gln Lys Ala Leu Ile Leu Leu Gly Leu Gln Lys Tyr Gln Glu
                610                 615                 620

Ala Leu Asp Glu Leu Glu Arg Leu Lys Glu Ile Ala Pro His Glu Ser
625                 630                 635                 640

Ser Met Tyr Ala Leu Met Gly Lys Ile Tyr Lys Gln Leu Asn Ile Leu
                645                 650                 655

Asp Lys Ala Val Phe Cys Phe Gly Ile Ala Leu Asp Leu Lys Pro Pro
                660                 665                 670

Ala Ala Asp Leu Ala Ile Ile Lys Ser Ala Met Glu Lys Val His Leu
675                 680                 685

Pro Asp Glu Leu Met Glu Asp Asp Leu
        690                 695

<210> SEQ ID NO 9
<211> LENGTH: 586
<212> TYPE: DNA
<213> ORGANISM: Zea mays

<400> SEQUENCE: 9
acagcttgac tcaagatttg catatgctca cactctatgt ggtcatgagt attctgcact      60
ggaggattat gagaatagta tcaaattcta cagatgtgca ctgcaggtag atgaaaggca    120
ctacaatgct tggtatggcc ttggggtggt gtatcttcgc caggaaaagt ttgagtttgc    180
tgagcatcat ttcagaaggg catttcagat aaatcctcgc tcttctgttc tcatgtgcta    240
tcttgggatg gccttgcatt ctcttaagag gaatgaagag gcactggaaa tgatggagaa    300
agctatagca gctgataaga gaatccact gcccaagtat cagaagtcct taattcttct    360
aggactaatg aagtatgaag aagctctgga tgagttggag cggctaaagg agattgcacc    420
tcatgagagt agtatgtatg cactgatggg aaagatttac aagcaactca atattcttga    480
caaagctgtt ttctgcttcg gcattgccct ggatttgaaa ccacctgctg ctgatcttgc    540
tataattaag tccgcaatgg agaaagtacc tcggccgcga ccacgc                   586

<210> SEQ ID NO 10
<211> LENGTH: 192
<212> TYPE: PRT
<213> ORGANISM: Zea mays
```

-continued

<400> SEQUENCE: 10

Gln Leu Asp Ser Arg Phe Ala Tyr Ala His Thr Leu Cys Gly His Glu
1               5                   10                  15

Tyr Ser Ala Leu Glu Asp Tyr Glu Asn Ser Ile Lys Phe Tyr Arg Cys
            20                  25                  30

Ala Leu Gln Val Asp Glu Arg His Tyr Asn Ala Trp Tyr Gly Leu Gly
        35                  40                  45

Val Val Tyr Leu Arg Gln Glu Lys Phe Glu Phe Ala Glu His His Phe
    50                  55                  60

Arg Arg Ala Phe Gln Ile Asn Pro Arg Ser Ser Val Leu Met Cys Tyr
65                  70                  75                  80

Leu Gly Met Ala Leu His Ser Leu Lys Arg Asn Glu Glu Ala Leu Glu
                85                  90                  95

Met Met Glu Lys Ala Ile Ala Ala Asp Lys Lys Asn Pro Leu Pro Lys
            100                 105                 110

Tyr Gln Lys Ser Leu Ile Leu Leu Gly Leu Met Lys Tyr Glu Glu Ala
        115                 120                 125

Leu Asp Glu Leu Glu Arg Leu Lys Glu Ile Ala Pro His Glu Ser Ser
    130                 135                 140

Met Tyr Ala Leu Met Gly Lys Ile Tyr Lys Gln Leu Asn Ile Leu Asp
145                 150                 155                 160

Lys Ala Val Phe Cys Phe Gly Ile Ala Leu Asp Leu Lys Pro Pro Ala
                165                 170                 175

Ala Asp Leu Ala Ile Ile Lys Ser Ala Met Glu Lys Val Pro Arg Pro
            180                 185                 190

<210> SEQ ID NO 11
<211> LENGTH: 344
<212> TYPE: DNA
<213> ORGANISM: Sorghum bicolor

<400> SEQUENCE: 11
ctccacaaca atcagccata tgctgcatac cacattttga aagggaagaa gatgccggag    60
tcccggtact tgtttgctac atcatgtttt cgaatgaacc tcttgcgtga agcagaagaa   120
actctatgtc cagtcaatga accaaacatg gaggttccaa gtggagcaac aggacactac   180
ctccttggag tgatttacag gtgcacaggc agaatttcag ctgcagctga acaatttaca   240
caagcgttga ctctagatcc tcttttatgg gcggcatatg aggaattgtg tatattaggt   300
attgctgaag ataccgatga gtgttttagt gaatcgactg ctct                    344

<210> SEQ ID NO 12
<211> LENGTH: 114
<212> TYPE: PRT
<213> ORGANISM: Sorghum bicolor

<400> SEQUENCE: 12

Leu His Asn Asn Gln Pro Tyr Ala Ala Tyr His Ile Leu Lys Gly Lys
1               5                   10                  15

Lys Met Pro Glu Ser Arg Tyr Leu Phe Ala Thr Ser Cys Phe Arg Met
            20                  25                  30

Asn Leu Leu Arg Glu Ala Glu Glu Thr Leu Cys Pro Val Asn Glu Pro
        35                  40                  45

Asn Met Glu Val Pro Ser Gly Ala Thr Gly His Tyr Leu Leu Gly Val
    50                  55                  60

Ile Tyr Arg Cys Thr Gly Arg Ile Ser Ala Ala Ala Glu Gln Phe Thr

```
            65                  70                  75                  80
Gln Ala Leu Thr Leu Asp Pro Leu Leu Trp Ala Ala Tyr Glu Glu Leu
                    85                  90                  95

Cys Ile Leu Gly Ile Ala Glu Asp Thr Asp Glu Cys Phe Ser Glu Ser
                100                 105                 110

Thr Ala

<210> SEQ ID NO 13
<211> LENGTH: 715
<212> TYPE: DNA
<213> ORGANISM: Triticum aestivum
<220> FEATURE:
<221> NAME/KEY: misc_feature
<222> LOCATION: (26)..(26)
<223> OTHER INFORMATION: n is any nucleotide

<400> SEQUENCE: 13
acccacgcgt ccgcacgaat attctngcat tggaggatta cgagaacagt gttaaattct      60
accgatgtgc acttcaggta gatgaaaggc actacaatgc ctggtatggg cttggagtag     120
tttaccttcg ccaggaaaag tttgagtttg ctgagcatca ttttagaagg gcatttcaga     180
taaatccccg ctcttctgtt cttatgtgct atcttgggat ggccttacat gctctaaaga     240
gagatgagga tgcattggag atgatggaga agccatatt ttctgataag aagaatccac      300
ttcctaagta tcagaaggct ttaattctgg taggccttca aaaatatcag gaggctctgg     360
atgagttgga acggctaagg gagattgcac ctcatgagag tagtatgtat gcacttatgg     420
gcaagatata caagcaactc aatattctcg acaaggctgt attttgcttt ggcgttgccc     480
ttgatttgaa acctcccgct gccgaccttg ctataatcaa gtctgcaatg gagaaagtac     540
accttccaga tgaactgatg gaggatgatg acctgtaagt tcactttaaa gcacaaactg     600
agaaatggac atttattcag atctatgagt ttctgcttgt gcttccgagt catggcctga     660
atgtgctttc ggagaggaac tcagaggttg aaggaagcaa gcacatcatg cggaa          715

<210> SEQ ID NO 14
<211> LENGTH: 181
<212> TYPE: PRT
<213> ORGANISM: Triticum aestivum

<400> SEQUENCE: 14

Ala Leu Glu Asp Tyr Glu Asn Ser Val Lys Phe Tyr Arg Cys Ala Leu
1               5                   10                  15

Gln Val Asp Glu Arg His Tyr Asn Ala Trp Tyr Gly Leu Gly Val Val
                20                  25                  30

Tyr Leu Arg Gln Glu Lys Phe Glu Phe Ala Glu His His Phe Arg Arg
            35                  40                  45

Ala Phe Gln Ile Asn Pro Arg Ser Ser Val Leu Met Cys Tyr Leu Gly
        50                  55                  60

Met Ala Leu His Ala Leu Lys Arg Asp Glu Asp Ala Leu Glu Met Met
65                  70                  75                  80

Glu Lys Ala Ile Phe Ser Asp Lys Lys Asn Pro Leu Pro Lys Tyr Gln
                85                  90                  95

Lys Ala Leu Ile Leu Val Gly Leu Gln Lys Tyr Gln Glu Ala Leu Asp
                100                 105                 110

Glu Leu Glu Arg Leu Arg Glu Ile Ala Pro His Glu Ser Ser Met Tyr
            115                 120                 125

Ala Leu Met Gly Lys Ile Tyr Lys Gln Leu Asn Ile Leu Asp Lys Ala
        130                 135                 140
```

```
Val Phe Cys Phe Gly Val Ala Leu Asp Leu Lys Pro Pro Ala Ala Asp
145                 150                 155                 160

Leu Ala Ile Ile Lys Ser Ala Met Glu Lys Val His Leu Pro Asp Glu
                165             170                 175

Leu Met Glu Asp Asp
            180
```